US 12,304,926 B2

(12) United States Patent
Ghorbani et al.

(10) Patent No.: US 12,304,926 B2
(45) Date of Patent: May 20, 2025

(54) METHODS AND SYSTEMS FOR RECOVERING PROTEIN POWDER AND NATURAL OMEGA-3 OIL FROM ANIMAL TISSUE

(71) Applicant: Advance International Inc., Livermore, CA (US)

(72) Inventors: Shahmard Maziar Ghorbani, Alamo, CA (US); Kerry Coltun, Alamo, CA (US)

(73) Assignee: Advance International Inc., Livermore, CA (US)

( * ) Notice: Subject to any disclaimer, the term of this patent is extended or adjusted under 35 U.S.C. 154(b) by 182 days.

(21) Appl. No.: 17/180,464

(22) Filed: Feb. 19, 2021

(65) Prior Publication Data

US 2022/0009962 A1 Jan. 13, 2022

Related U.S. Application Data

(63) Continuation of application No. 15/173,448, filed on Jun. 3, 2016, now abandoned.
(Continued)

(51) Int. Cl.
*C07K 1/36* (2006.01)
*A23J 1/04* (2006.01)
(Continued)

(52) U.S. Cl.
CPC ............ *C07K 1/36* (2013.01); *A23J 1/04* (2013.01); *C11B 1/10* (2013.01); *C11B 1/108* (2013.01);
(Continued)

(58) Field of Classification Search
CPC ...... B01D 53/04; B01D 53/00; B01D 33/056; B01D 45/02; C11B 3/16
See application file for complete search history.

(56) References Cited

U.S. PATENT DOCUMENTS

| 81,987 A | 9/1868 | Cutler |
| 2,679,457 A | 5/1954 | Shaw |

(Continued)

FOREIGN PATENT DOCUMENTS

| CA | 891977 A | 2/1972 |
| CN | 1683397 A | 10/2005 |

(Continued)

OTHER PUBLICATIONS

Asia-Pacific Fishery Commission, "Bread Formulation," Jun. 1996, Summary Report of and Papers Presented at the Tenth Session of the Working Party of Fish Technology and Marketing, pp. 280-281.
(Continued)

*Primary Examiner* — Sharon Pregler
(74) *Attorney, Agent, or Firm* — SNELL & WILMER L.L.P.

(57) ABSTRACT

Provided are methods and systems for recovering protein product powder, purified water and omega-3 oil from an animal tissue. The methods and systems use high throughput extraction filtration separation systems. Animal tissue, for example fish, and organic solvent are directly or indirectly transferred into one of the optional extraction or filtration systems. The extraction-filtration systems provide a high degree of filtration performance and product washing efficiency. Each system ultimately yields a product wet cake that includes the protein product. The protein product wet cake is then further dried in a drying unit to yield the final protein powder product. In each system, the process filtrates undergo further processing by filtration and distillation to recover the organic solvent and separate out the omega-3 fish oil. The recovered organic solvent can be recycled back into the process. Solid protein product powder is thus recovered, along with omega-3 oil, purified water and recovered solvent.

10 Claims, 6 Drawing Sheets

Related U.S. Application Data

(60) Provisional application No. 62/171,173, filed on Jun. 4, 2015.

(51) Int. Cl.

| | | |
|---|---|---|
| C11B 1/10 | (2006.01) | |
| C11B 1/12 | (2006.01) | |
| C11B 3/00 | (2006.01) | |
| C11B 3/16 | (2006.01) | |
| C11B 13/00 | (2006.01) | |

(52) U.S. Cl.
    CPC ............. C11B 1/12 (2013.01); C11B 3/001 (2013.01); C11B 3/16 (2013.01); C11B 13/00 (2013.01); *Y02W 30/74* (2015.05)

(56) References Cited

U.S. PATENT DOCUMENTS

| | | |
|---|---|---|
| 2,680,754 A | 6/1954 | Stapelberg |
| 2,746,168 A | 5/1956 | Rickabaugh |
| 2,875,061 A | 2/1959 | Vogel et al. |
| 3,076,708 A | 2/1963 | Cavanagh et al. |
| 3,200,105 A | 8/1965 | Barber et al. |
| 3,252,962 A | 5/1966 | Whaley et al. |
| 3,357,798 A | 12/1967 | Hachiro et al. |
| 3,520,868 A | 7/1970 | Henderson et al. |
| 3,615,657 A | 10/1971 | Gastrock et al. |
| 3,649,294 A | 3/1972 | Thijssen |
| 3,659,294 A | 5/1972 | Glabiszewski |
| 3,697,285 A | 10/1972 | Faith, Jr. et al. |
| 3,835,041 A | 9/1974 | Grant |
| 3,836,686 A | 9/1974 | Roels et al. |
| 3,852,260 A | 12/1974 | Knutsen et al. |
| 3,898,745 A | 8/1975 | Carlsson |
| 3,943,233 A | 3/1976 | Swanson et al. |
| 4,118,285 A | 10/1978 | Yeh |
| 4,144,229 A | 3/1979 | Karnofsky |
| 4,213,941 A | 7/1980 | Boomer |
| 4,246,184 A | 1/1981 | Pressick et al. |
| 4,266,473 A | 5/1981 | Hunt et al. |
| 4,277,411 A | 7/1981 | Yahl |
| 4,298,162 A | 11/1981 | Hohne |
| 4,335,146 A | 6/1982 | Bladh |
| 4,405,649 A | 9/1983 | Jeffreys et al. |
| 4,405,653 A | 9/1983 | Gray |
| 4,406,831 A | 9/1983 | Atteck |
| 4,441,797 A | 4/1984 | Maruyama et al. |
| 4,566,873 A | 1/1986 | Toda |
| 4,595,501 A | 6/1986 | Queyroix |
| 4,623,488 A | 11/1986 | Takao |
| 4,659,469 A | 4/1987 | Gaudfrin |
| 4,685,899 A | 8/1987 | Cvitas et al. |
| 4,707,369 A | 11/1987 | Suresky |
| 4,731,182 A | 3/1988 | High |
| 4,744,926 A | 5/1988 | Rice |
| 4,751,060 A | 6/1988 | Kratochwill |
| 4,790,806 A | 12/1988 | High |
| 4,797,474 A | 1/1989 | Patroni et al. |
| 4,820,528 A | 4/1989 | Stroz et al. |
| 4,820,529 A | 4/1989 | Uchida et al. |
| 4,825,541 A | 5/1989 | Czeschka et al. |
| 4,859,371 A | 8/1989 | Diosady et al. |
| 4,861,495 A | 8/1989 | Pietzsch |
| 4,871,560 A | 10/1989 | Brokans |
| 4,888,181 A | 12/1989 | Gray et al. |
| 4,976,973 A | 12/1990 | Shirakawa et al. |
| 5,047,004 A | 9/1991 | Wells |
| 5,053,234 A | 10/1991 | Anderson et al. |
| 5,097,017 A | 3/1992 | Konwinski |
| 5,175,355 A | 12/1992 | Streich et al. |
| 5,178,602 A | 1/1993 | Wells |
| 5,200,557 A | 4/1993 | Gee et al. |
| 5,257,968 A | 11/1993 | Caldwell |
| 5,261,869 A | 11/1993 | Caldwell et al. |
| 5,267,936 A | 12/1993 | Miachon |
| 5,342,279 A | 8/1994 | Cooperstein |
| 5,384,149 A | 1/1995 | Lin |
| 5,544,425 A | 8/1996 | Haleen |
| 5,614,102 A | 3/1997 | Sakurada |
| 5,643,468 A | 7/1997 | Ure |
| 5,658,462 A | 8/1997 | Hopkins et al. |
| 5,685,975 A | 11/1997 | Joubert et al. |
| 5,853,791 A | 12/1998 | Roussel |
| 5,958,233 A | 9/1999 | Willgohs |
| 5,972,403 A | 10/1999 | Tiller |
| 6,001,398 A | 12/1999 | Noda et al. |
| 6,005,073 A | 12/1999 | Hultin et al. |
| 6,042,872 A | 3/2000 | Kemme-Kroonsberg et al. |
| 6,055,936 A | 5/2000 | Collin |
| 6,136,959 A | 10/2000 | Hultin et al. |
| 6,162,477 A | 12/2000 | Crisinel et al. |
| 6,190,715 B1 | 2/2001 | Crowther et al. |
| 6,261,608 B1 | 7/2001 | Lee et al. |
| 6,288,216 B1 | 9/2001 | Hultin et al. |
| 6,290,383 B1 | 9/2001 | Shohet |
| 6,562,952 B1 | 5/2003 | Rajewski et al. |
| 6,634,508 B1 | 10/2003 | Ishigaki |
| 6,685,975 B2 | 2/2004 | Saxby et al. |
| 7,033,636 B2 | 4/2006 | Kelleher |
| 7,156,801 B2 | 1/2007 | Dircks et al. |
| 7,462,736 B2 | 12/2008 | Parker et al. |
| 7,470,370 B2 | 12/2008 | Parker et al. |
| 7,713,411 B2 | 5/2010 | Banister et al. |
| 7,763,717 B1 | 7/2010 | Jaczynski et al. |
| 7,888,530 B2 | 2/2011 | Lin et al. |
| 7,897,810 B2 | 3/2011 | Lin et al. |
| 7,956,081 B2 | 6/2011 | Kelleher |
| 8,152,708 B2 | 4/2012 | Ellsworth et al. |
| 8,173,014 B2 | 5/2012 | Soerensen et al. |
| 8,609,157 B2 | 12/2013 | Katevas et al. |
| 8,628,817 B2 | 1/2014 | Ramirez |
| 8,663,725 B2 | 3/2014 | Ortega et al. |
| 8,697,906 B2 | 4/2014 | Parker et al. |
| 8,772,516 B2 | 7/2014 | Sclabos et al. |
| 8,815,551 B2 | 8/2014 | Lihme |
| 8,828,447 B2 | 9/2014 | Soerensen et al. |
| 8,859,825 B2 | 10/2014 | Parker et al. |
| 8,865,236 B2 | 10/2014 | Sclabos et al. |
| 8,968,169 B2 | 3/2015 | Eiken |
| 9,011,942 B2 | 4/2015 | Sclabos et al. |
| 9,028,387 B2 | 5/2015 | Eiken |
| 9,150,815 B2 | 10/2015 | Sclabos et al. |
| 9,232,812 B2 | 1/2016 | Soerensen et al. |
| 9,706,787 B2 | 7/2017 | Ortega |
| 9,826,757 B2 | 11/2017 | Ghorbani et al. |
| 9,861,945 B1 | 1/2018 | Beetz et al. |
| 10,039,299 B2 | 8/2018 | Ghorbani et al. |
| 2002/0128325 A1 | 9/2002 | Runge et al. |
| 2002/0151733 A1 | 10/2002 | Ulrich et al. |
| 2003/0120095 A1 | 6/2003 | Rohr et al. |
| 2003/0215559 A1 | 11/2003 | Mikaelian et al. |
| 2004/0156882 A1 | 8/2004 | Davenport et al. |
| 2005/0129835 A1 | 6/2005 | Delahanty, Jr. |
| 2005/0244567 A1 | 11/2005 | Carlsson |
| 2005/0255228 A1 | 11/2005 | Kellher |
| 2006/0111578 A1 | 5/2006 | Arhancet et al. |
| 2006/0128665 A1 | 6/2006 | Leigh et al. |
| 2006/0241016 A1 | 10/2006 | Haines |
| 2006/0251793 A1 | 11/2006 | Junger |
| 2006/0258872 A1 | 11/2006 | Kase et al. |
| 2007/0134376 A1 | 6/2007 | Connell |
| 2008/0009650 A1 | 1/2008 | Sluijmers et al. |
| 2008/0066019 A1 | 3/2008 | Worek et al. |
| 2008/0226810 A1 | 9/2008 | Passe et al. |
| 2009/0061067 A1 | 3/2009 | Tilseth et al. |
| 2009/0238930 A1 | 9/2009 | Sathivel |
| 2010/0087935 A1 | 4/2010 | Pettus et al. |
| 2010/0092603 A1 | 4/2010 | Bruinsma et al. |
| 2010/0331580 A1 | 12/2010 | Ridgley |
| 2011/0217386 A1 | 9/2011 | Jansson et al. |
| 2011/0305817 A1 | 12/2011 | Cho et al. |
| 2011/0315621 A1 | 12/2011 | Heley et al. |
| 2012/0073184 A1 | 3/2012 | Cranford et al. |

(56) References Cited

U.S. PATENT DOCUMENTS

| | | |
|---|---|---|
| 2012/0190872 A1 | 7/2012 | Cranford et al. |
| 2014/0024064 A1 | 1/2014 | Burlew et al. |
| 2014/0073820 A1 | 3/2014 | Bazzana et al. |
| 2014/0148566 A1 | 5/2014 | Denkwitz et al. |
| 2014/0271045 A1 | 9/2014 | Swanson et al. |
| 2014/0272045 A1* | 9/2014 | Ghorbani .......... C11B 1/10 202/168 |
| 2014/0302086 A1 | 10/2014 | Kelly |
| 2014/0357815 A1 | 12/2014 | Denkwitz et al. |
| 2014/0370115 A1 | 12/2014 | Hoem et al. |
| 2015/0370115 A1 | 12/2015 | Ge et al. |
| 2016/0355546 A1 | 12/2016 | Ghorbani et al. |
| 2017/0311623 A1 | 11/2017 | Ortega |
| 2018/0289037 A1 | 10/2018 | Schweizer et al. |
| 2019/0021362 A1 | 1/2019 | Ghorbani et al. |
| 2020/0275678 A1 | 9/2020 | Ortega |
| 2021/0307355 A1 | 10/2021 | Ghorbani et al. |
| 2021/0386105 A1 | 12/2021 | Mentak et al. |

FOREIGN PATENT DOCUMENTS

| | | |
|---|---|---|
| CN | 101595939 A | 12/2009 |
| DE | 10160042 A1 | 6/2003 |
| EP | 0280415 A1 | 8/1988 |
| EP | 0301795 A1 | 2/1989 |
| EP | 2361513 A1 | 8/2011 |
| EP | 2319331 B1 | 8/2013 |
| EP | 2999350 B1 | 5/2018 |
| FR | 2168259 A1 | 8/1973 |
| FR | 2340055 A1 | 9/1977 |
| GB | 1156500 A | 6/1969 |
| JP | 2015155082 A * | 8/2015 |
| WO | WO-9740941 A1 | 11/1997 |
| WO | WO-0064567 A1 | 11/2000 |
| WO | WO-0220720 A2 | 3/2002 |
| WO | WO-2009102781 A1 | 8/2009 |
| WO | WO-2010030944 A3 | 10/2010 |
| WO | WO-2011051743 A1 | 5/2011 |
| WO | WO-2011075542 A1 | 6/2011 |
| WO | WO-2011094549 A1 | 8/2011 |
| WO | WO-2011156380 A2 | 12/2011 |
| WO | WO-2014145083 A2 | 9/2014 |
| WO | WO-2014145083 A3 | 11/2014 |
| WO | WO-2016197057 A1 | 12/2016 |
| WO | WO-2020023557 A1 | 1/2020 |
| WO | WO-2021150794 A1 | 7/2021 |

OTHER PUBLICATIONS

Barlow et al., "Fishery By-Products," International Association of Fish Meal Manufacturers, CRS Handbook of Nutritional Supplements No. 19 (1984): 1-23.
Bose et al., Coastal Aquaculture Engineering, Great Britain, distributed by Routledge, Chapman and Hall, Inc., 1991, ISBN 0-7131-2947-6, pp. 345 and 350.
European Application No. EP14764069.2 European Search Report dated Aug. 10, 2016.
European Application No. EP16804601.9, Extended European Search Report dated Dec. 11, 2018.
European Application No. EP18158983.9, Extended European Search Report dated Sep. 28, 2018.
FAO Fishery Industries Division, "The Production of Fish Meal and Oil," Jan. 2007, retrieved from the Internet: URL: http://web.archive.org/web/20070105042516/http://www.fao.org/docrep/003/x6899e/x6899e04.htm.
Geirsdottir, M. Protein Isolation from Herring. Norden Nordic Innovation Centre, Icelandic Fisheries Laboratories, (2005): 1-118.
Kristinsson et al., "Fish Protein Hydrolysates: Production, Biochemical, and Functional Properties," Critical Reviews in Food Science and Nutrition 40(1): 43-81 (2000).
Liston et al. "Fish Protein Concentrate," Institute for Food Science and Technology, University of Nashington, Seattle, Washington (1970): 285-289.

Nurdiyana et al., "Optimization of Protein Extraction From Freeze Dried Fish Waste Using Response Surface Methodology (RSM)," International Journal of Engineering and Technology, vol. 5, No. 1, (2008): 48-56.
PCTUS14/029748 International Search Report and Written Opinion dated Sep. 2, 2014.
PCT/US2010/060602 International Search Report and Written Opinion dated Feb. 14, 2011.
PCT/US/2016/035908 International Search Report and Written Opinion dated Sep. 27, 2016.
Romadhoni, et al. Extraction of Snakehead Fish [*Ophiocephalus straitus* (Bloch, 1793)] Into Fish Protein Concentrate as Albumin Source Using Various Solvent, Jumal Teknologi, Penerbit UTM Press, vol. 78, No. 4-2, (2016): p. 1-6.
Saha, Extraction of Protein from Hoki and Barracouta Fish Heads for Utilisation as Functional Ingredients, A thesis presented in partial fulfilment of the requirements for the degree of Master of Food Technology at Massey University, Palmerston North, New Zealand (2014): 1-163.
Shaviklo, Development of Fish Protein Powder as an Ingredient for Food Applications: A Review, J Food Sci Technol, Springer, vol. 52, No. 2 (2015): 648-661.
Stillings et al., Fish Protein Concentrate: A New Source of Dietary Protein, Journal of the American Oil Chemists Society, vol. 48(8), pp. 412-414 (1971).
U.S. Appl. No. 11/973,106 Notice of Allowance dated Dec. 20, 2013.
U.S. Appl. No. 11/973,106 Office Action dated Aug. 24, 2010.
U.S. Appl. No. 11/973,106 Office Action dated Mar. 10, 2011.
U.S. Appl. No. 11/973,106 Office Action dated Oct. 3, 2012.
U.S. Appl. No. 12/639,946 Notice of Allowance dated Mar. 17, 2017.
U.S. Appl. No. 12/639,946 Office Action dated Apr. 2, 2012.
U.S. Appl. No. 12/639,946 Office Action dated Dec. 18, 2012.
U.S. Appl. No. 12/639,946 Office Action dated Jan. 7, 2015.
U.S. Appl. No. 12/639,946 Office Action dated Jun. 29, 2016.
U.S. Appl. No. 12/639,946 Office Action dated Jun. 4, 2014.
U.S. Appl. No. 12/639,946 Office Action dated Sep. 1, 2015.
U.S. Appl. No. 14/052,514 Final Office Action dated Feb. 24, 2016.
U.S. Appl. No. 14/052,514 Notice of Allowance dated Jun. 12, 2017.
U.S. Appl. No. 14/052,514 Office Action dated Aug. 5, 2015.
U.S. Appl. No. 14/052,514 Office Action dated Oct. 6, 2016.
U.S. Appl. No. 15/173,448 Office Action dated Apr. 18, 2019.
U.S. Appl. No. 15/173,448 Office Action dated Jun. 21, 2018.
U.S. Appl. No. 15/651,755 Office action dated Apr. 2, 2019.
U.S. Appl. No. 15/651,755 Office Action dated Jul. 24, 2018.
U.S. Appl. No. 15/651,755 Office Action dated Sep. 6, 2017.
U.S. Appl. No. 15/803,115 Notice of Allowance dated May 24, 2018.
U.S. Appl. No. 15/803,115 Office Action dated Feb. 13, 2018.
U.S. Appl. No. 15/651,755 Office Action dated Mar. 21, 2018.
Weiyi, W. Solid-Liquid Separation Technology and Energy Saving. Chemical Equipment Technology, Issue 2 (1984).
Windsor, Fish Protein Concentrate, Nov. 2002, retrieved from the Internet: URL: http://web.archive.org/web/20021118202451.
Green Facts, Scientific Facts on Boron. retrieved from Internet: http://web.archive.org/web/20060930055328/ http://www.greenfacts.org/en/boron/l-3/boron-3.htm#1 (2006).
Laihao, Li et al. Studies on the Extraction of Fish Protein Concentrate (FPC) by Solvent Extraction FAO, Bangkok, Thailand (1998) pp. 114-118.
Nabrzyski, M, and R Gajewska. Content of strontium, lithium and calcium in selected milk products and in some marine smoked fish. Die Nahrung vol. 46,3 (2002): 204-8.
PCT/US2019/043120 International Search Report and Written Opinion dated Oct. 1, 2019.
PCT/US2021/014472 International Search Report and Written Opinion dated May 12, 2021.
U.S. Appl. No. 16/591,424 Final Office Action dated Feb. 3, 2023.
Hokin et al., Analysis of the Cobalt Content in Australian Foods, Asia Pac J Clin Nutr, 13 (3), pp. 284-288 (2004).

(56) References Cited

OTHER PUBLICATIONS

Nielsen, F H. How should dietary guidance be given for mineral elements with beneficial actions or suspected of being essential ?. The Journal of nutrition vol. 126,9 Suppl (1996): 2377S-2385S. doi:10.1093/jn/126.suppl_9.2377S.
U.S. Appl. No. 16/591,424 Office Action dated Mar. 31, 2022.
U.S. Appl. No. 17/097,691 Office Action dated Sep. 7, 2022.

* cited by examiner

METHODS AND SYSTEMS FOR RECOVERING PROTEIN POWDER AND NATURAL OMEGA-3 OIL FROM ANIMAL TISSUE

RELATED APPLICATION

This application is a continuation of, claims priority to and the benefit of, U.S. application Ser. No. 15/173,448 titled "Methods And Systems For Recovering Protein Powder And Natural Omega-3 Oil From Animal Tissue," filed Jun. 3, 2016. The '448 application claims benefit of and priority to U.S. Provisional Application No. 62/171,173 to SHAHMARD MAZIAR GHORBANI and KERRY COLTUN, titled "METHODS AND SYSTEMS FOR RECOVERING PROTEIN POWDER AND NATURAL OMEGA-3 OIL FROM ANIMAL TISSUE," filed Jun. 4, 2015, the subject matter of which is incorporated by reference in its entirety.

This application is related to International PCT Application No. PCT/US2016/035908, filed Jun. 3, 2016, entitled "METHODS AND SYSTEMS FOR RECOVERING PROTEIN POWDER AND NATURAL OMEGA-3 OIL FROM ANIMAL TISSUE," which also claims priority to U.S. Provisional Application Ser. No. 62/171,173. The subject matter of the above-noted International application is incorporated by reference in its entirety.

FIELD

The present invention relates generally to methods and systems for producing a concentrated low-moisture piscine or marine animal protein powder concentrate and natural omega-3 oil for human consumption. The methods and systems provide for recovering protein product powder, natural omega-3 oil and water from any type of fresh or frozen piscine or marine animal or eggs or parts thereof, or from dehydrated fishmeal and/or commodity dried fish, as starting raw materials. The general methodology involves the use of an extraction solvent in conjunction with several equipment system options that can be used independently or in various combinations. The methods and systems provide a recovery mechanism that allows reuse of the extraction solvent efficiently and cost effectively. The recovered protein powder, omega-3 oil and water can be used in many applications, for example, as main ingredients in food manufacturing, nutritional supplement products, hunger relief packages, cosmetics, and high quality pet foods. The recovered water also can be used as a beverage, for use in brewing and for industrial applications. The process also can yield an all-natural liquid fertilizer. The recovered water, which can be recovered via distillation or membrane filtration or combinations thereof, typically contains little or no ions. The recovered water can be similar to desalinized water. It should be noted that the methods and systems of the present invention can be used with any animal tissue, although preferably, the methods and systems are used in conjunction with almost any fish and fish bi-catch and recyclable fresh fish parts, as this source of raw material is a plentiful and sustainable resource. The protein powder, omega-3 oil and purified water are fit for human consumption.

The systems and methods can be land-based or used on marine vessels. In some applications, the systems are configured for installation and use on a marine vessel. For example, the system can be configured to fit within the confines of a portion of a lower deck of the vessel. Modules of the system can be configured to be removably fixed to a wall or deck of the vessel. A lateral dampening attachment can be used between modules or between a module and a fixed surface, such as the deck or a wall, to minimize lateral movement which could be caused by movement of the vessel, e.g., due to ocean waves.

More specifically, given the mounting world food shortage problems in many areas of the globe, the present invention provides a methodology for producing a high quality protein supplement, which can provide a means to combat the ever growing malnutrition crisis. The protein supplement can be derived from a wide variety of optional 100% natural resources, such as small, short lived, fresh and plentiful ocean fish. These resources are considered green and sustainable and are an excellent renewable natural resource. Their use will combat overfishing of certain species, and help balance the oceanic ecosystem by reducing the environmental impact due to discarded fresh fish parts and carcasses generated by the fish processing industries. Environmental benefits are realized by recycling these otherwise discarded fresh fish materials using the methods and systems provided herein. In an age where there is a growing requirement for green and environmentally conscientious processing, the ability to reuse and recycle fresh and nutritionally valuable waste materials generated by the general fishery industry affords a certain unique benefit to the current invention.

RELATED ART

A number of processes are available for recovering protein from fish or marine animal tissue (e.g., see U.S. Pat. Nos. 4,405,649; 4,976,973; and 5,972,403). In these wet processes, fish are treated with acids, proteases or high temperatures or combinations thereof before or after grinding the fish in blenders. In a different process (e.g., see U.S. Pat. No. 8,663,725), the fish tissue is processed using an organic solvent to produce a slurry. The resulting slurry contains recoverable solid particles of tissue that contain protein and crude omega-3 oil.

While animal tissue purification systems and techniques already exist in the marketplace, one major setback is the efficiency in recovering products. Inefficiencies generally are attributed to downtime caused by equipment maintenance and replacement. For example, equipment inlets and outlets, as well as conduits for transferring product, may become clogged and create obstructions to material flow. Also, employing many pieces of equipment in the purification system requires additional labor hours to individually inspect each piece of equipment prior to verifying the system is appropriate for further processing. What is desired in the art is a more efficient system and process for purifying animal tissue to meet present consumer demands. Also desired is a system and process for improving yield of recovered products from animal tissue. Further desired is a system and process for recovering products with long shelf-lives. What is further desired is a solvent recycling system that recycles the organic solvent, and thus reduces the usage of the organic solvent and the volatile organic compound (VOC) emissions of organic solvent into the atmosphere.

Various techniques have been used for isolating solid product materials from a slurry. Examples of such techniques include separation by gravity by maintaining the slurry in a holding tank for extended periods of time, filtration, and centrifugation systems. Filtration systems typically employ a filter media through which the liquid phase of the slurry is drawn, using only gravity or a combination of vacuum to draw the liquid through the filter in conjunction with gas pressure to force the liquid phase through the solid cake and filter media. The result is a protein powder filter cake on the filter media which is further dried. Batch filtration and centrifugation systems have a high capital cost and a limited product throughput that can prove challenging for meeting market demands in a cost effective manner. Additional costs and possible loss of product during material transfer to a suitable drying unit also can occur with use of typical centrifugation or batch filtration systems.

Accordingly, a need exists for methods and systems that more efficiently produce protein powder for piscine and marine animals.

SUMMARY OF THE INVENTION

Accordingly, the present invention is directed to improved methods and systems for producing protein powder concentrate, natural omega-3 oils and purified water that substantially obviate one or more of the problems due to limitations and disadvantages of the related art.

The objectives of the systems and methods provided herein include providing more efficient systems and methods for recovering nutritionally superior products from animal tissue with a substantially increased production rate in an environmentally friendly and socially responsible manner. The animal tissue can be raw fish. The raw fish can be any kind of fish and any part of the fish, including sustainable abundant species of fish and fish parts that are ordinarily considered waste by the fish processing industries.

Malnutrition is an issue in developing countries having inadequate techniques and resources for storing perishable foods. Namely, modern technological advances, such as refrigeration systems, come at a price few can afford in remote, impoverished areas. While water may be one of earth's most abundant resources, obtaining purified drinking water still poses a challenge for millions of people living in developing countries. One reason may be attributed to the proximity to available water sources, e.g., landlocked countries and countries in proximity to bodies of salt water, but not fresh water. Even if proximity is of no concern, financial constraints in developing countries may result in the lack of readily available, efficient water purification systems. The present invention allows for the recovery of water from the process, where the recovered water is purified for drinking and human consumption.

One solution is to extract vital resources from animal tissue. Whether landlocked or next to the sea, many developing countries have access to an abundant supply of land or marine animals. Marine animals, more specifically fish, are made up of resources including protein, fish oils including omega-3, and water derived from the fish itself. In view of the techniques employed by the present invention to recover these products, the shelf-life can be extended. By so doing, the necessity to preserve perishable goods via refrigeration is reduced and/or eliminated.

The present invention proposes several unique and first of a kind technologies to produce a highly pure and stable protein product powder that contains levels of desirable minerals such as calcium, potassium, zinc and other required inorganic materials. These constituents are naturally derived from bones and flesh that are associated with, for example, raw fish ingredients. The resultant protein product powder is a complete protein source comprising all of the essential amino acids, whose composition is further complemented by naturally occurring inorganic mineral substances. The nature of the technology utilizes pharmaceutical grade processing systems and unit operations to ensure final protein product purity and compliance with the manufacturing requirements that are imposed in a regulated industry.

An advantage of the present invention is to provide green, sustainable processes, methods and systems for recovery of protein and omega-3 oils from piscine and marine animal tissue. The recovered protein is non-hygroscopic, having been tested to exhibit a shelf-stable for at least 5 years. In the methods and systems provided herein, the piscine or marine animal flesh is not subjected to thermal excesses or treated with acids or enzymes as pre-digestion measures prior to separating the omega-3 oils from the protein-containing particles. Another advantage of the present invention is the recovered protein product is rapidly digestible and has a superior amino acid content and profile compared to other available bulk manufactured protein sources. For example, Table 1 shows a comparison of the powdered protein product produced using the systems and methods provided herein compared to other plant based and alternate bulk proteins.

The recovered protein associated with this invention has a 98% digestibility, contains natural minerals, and is lower in fat and cholesterol than other animal proteins, such as whey, beef, and chicken. In some embodiments, the powdered protein product can contain less than about 0.1 wt % or less than 0.05 wt % trans fatty acid isomers per 100 gram serving. In some embodiments, the powdered protein product can contain less than about 0.1 wt %, or less than about 0.05 wt %/o, or less than about 0.02 wt % cholesterol per 100 gram serving.

The recovered protein can be non-GMO (Genetically Modified Organism), gluten free, odorless and tasteless, and contains no measurable heavy metals. The recovered protein exhibits a very long shelf life of 5 years, and is very stable for storage and manufacturing equipment friendly due to its non-hygroscopic nature.

Another advantage of the present invention is the level of zero grain requirements, thus eliminating the need for sacrificing land that is otherwise required for the production of important agricultural based food sources. The fish sources make use of sustainable small fish, thus giving rise to a superior nutritional profile. In comparison with land based derived products, the protein recovered in accordance with this invention can have a much lower carbon footprint and requires no raw materials (e.g., grains and water) for feeding the fish sources (see Table 2).

TABLE 1

Comparison of Recovered Protein with Alternate Recovered Proteins
Standardized to 25 grams of protein per serving

|  | Powdered Protein Product | Blue Wave | Source Organic Whey | American Whey | Bulk Food Whey Isolate | NutriBio Whey Isolate | NutraBio Soy Protein Isolate | BulkFood Soy Protein Isolate |
|---|---|---|---|---|---|---|---|---|
| Serving Size | 29.2 |  | 29.8 | 28.5 | 27.5 | 28.3 | 28.7 | 27.5 |
| Calories | 100.0 | 135.0 | 119.0 | 104.0 | 128.8 | 107.0 | 110.0 | 128.8 |

TABLE 1-continued

Comparison of Recovered Protein with Alternate Recovered Proteins
Standardized to 25 grams of protein per serving

|  | Powdered Protein Product | Blue Wave | Source Organic Whey | American Whey | Bulk Food Whey Isolate | NutriBio Whey Isolate | NutraBio Soy Protein Isolate | BulkFood Soy Protein Isolate |
|---|---|---|---|---|---|---|---|---|
| Protein | 25.0 | 25.0 | 25.0 | 25.0 | 25.0 | 25.0 | 25.0 | 25.0 |
| Carbohydrates | 0.3 | 3.0 | 2.4 | 1.4 | 1.3 | 1.0 | 0.0 | 0.0 |
| Fat in gm | 0.0 | 2.1 | 1.8 | 0.0 | 0.6 | 1.0 | 1.0 | 1.3 |
| Saturated Fats | 0.0 | 2.1 | 0.6 | 0.0 | NA | 1.0 | NA | NA |
| Cholesterol | 0.0 | 31.3 | 47.6 | 4.5 | NA | 2.0 | NA | NA |
| Shelf Life | 5 years | 2 years | 2 years | 2 years | 2 years | 2 years | 2 years | 2 years |
| Taste | NONE | strong fish | mild milk | mild milk | mild | mild milk | mild soy | mild soy |
| Odor | NONE | strong fish | mild milk | mild milk | mild | mild milk | mild | mild |
| GMO | NO | no | no | yes (feed) | yes (feed) | yes (feed) | yes (seed) | yes (seed) |

TABLE 2

Requirements & Carbon Footprint of Alternate Protein Sources

| Requirement of 1 Pound of: | Grain (Lbs) | Water (Gallons) | Carbon Foot Print (Kg $CO_2$/Kg edible product) |
|---|---|---|---|
| Pork | 6 | 3,500 | 3-6 |
| Chicken | 2.3 | 2,000 | 1.5-7 |
| Beef (whey) | 13 | 2,500 | 16-40 |

Another advantage of the present invention is the product's general positive effect on human health compared to alternate plant based protein sources. For example, 93% of US grown soy can be genetically modified which some people believe may be related to serious health risks, such as toxicity, allergenicity, antibiotic resistance, immune-suppression, cancer risks, and possible goitrogenic [thyroid] and carcinogenic effects. A contributor to these deleterious effects is believed to be farming methods using GMO technologies that can promote treatments with herbicides and pesticides. Similarly, protein sources derived from animal based processes (e.g., beef) can be subjected to hormone and animal antibiotic treatments.

Another advantage of the present invention is that the systems provided herein require a small footprint for manufacturing the recovered protein, where the required equipment can be contained on compact automated manufacturing modules. These modules typically can have a smaller footprint than comparable food manufacturing factories. These manufacturing modules can be easily transported to multiple locations and deployable around the globe, within close proximity to the source of raw materials, including marine vessels, fish processing vessels and mother ship vessels (a ship providing facilities and supplies for a number of smaller vessels).

The systems can configured for installation and use on a marine vessel. For example, the system can be configured to fit within the confines of a portion of a lower deck of the vessel. Modules of the system can be configured to be removably fixed to a wall or deck of the vessel, and appropriately sized for ease of placement within the vessel. The connections between modules or between a module and a fixed surface, such as a wall of deck floor, or both, can be selected to minimize displacement of the modules of the system due to the motion of the vessel through the water. For example, a lateral dampening attachment can be used between modules or between a module and a fixed surface, such as the deck or a wall, or both, in order to minimize lateral movement which could be caused by movement of the vessel or due to ocean waves or a combination thereof. A further dampening member can be used to damp vertical or heave forces to limit the maximum vertical displacement of the modules. The dampening members independently can be controlled in order to independently address the separate forces acting on the module(s). The separate control can allow for the overall response of the dampening members(s) to be more accurately tailored to address the conditions in the vessel. Any arrangement for permitting limited movement, such as springs, hydraulic cylinders, electronic suspension systems, adaptive suspension systems, rubber bumpers or connectors, or inter-coupling devices that permit satisfactory coupling of the modules to each other or to a fixed surface while allowing sufficient freedom of movement can be used, alone or in combination.

Provided herein are methods and apparatus for producing a low-moisture protein (less than 5 wt % moisture, e.g., less than 1 wt % moisture, or less than 0.5 wt % moisture) product concentrate and purified low heat (temperature range 45° C.-72° C.) processed, omega-3 oils for human consumption from piscine or marine animals or eggs or parts thereof, or from dehydrated fishmeal or commodity dried fish, or combinations thereof, as starting raw materials.

Another embodiment of the present invention concerns a method for producing a protein product in the form of a low moisture wet cake containing solid particles of protein. The method comprises: (a) introducing a slurry containing a solid phase that includes solid particles containing protein and a liquid phase containing an organic solvent and omega-3 oil into a product recovery system; (b) separating the slurry into a liquid phase and an isolated solid phase, where the solid phase is in the form of an initial wetcake; (c) washing the initial wetcake with a product wash stream having a temperature within the range of 25° C. to 72° C. to produce a washed wetcake and a wash filtrate; and (d) drying the washed wetcake to produce the final protein product.

In the methods and processes provided herein, the solvent can be reclaimed from the wash filtrate and the slurry extraction filtrate, where both filtrates are collected and recycled for subsequent reuse in the process.

Also provided are methods for isolating solid protein product and omega-3 oil from a slurry mixture containing a solvent and ground piscine or marine animal tissue. The methods include treating a slurry that includes solid particles of ground tissue and a liquid phase that includes a solvent and an oil fraction. This mixture is processed within a product recovery system to separate the slurry, thus producing an isolated liquid phase and a low-moisture wet cake substantially containing protein. In the methods provided herein, treatment of the slurry can include depositing the slurry on a surface of a filter, wherein the solid particles are retained on the surface of the filter, and washing at least a portion of the solid particles with a wash stream having a temperature within the range of 25 to 72° C., thus forming a wet cake containing the solid particles which are of substantially recovered protein. The filter can be part of one of several types of separation systems, e.g., a vacuum belt filtration system, or an immersion extractor, or a percolation extractor, or a rotary drum filter, a screw press, a decanter centrifuge, or a combination thereof. The wetcake can be processed to further remove liquid through the use of a drying system.

In the methods provided herein, omega-3 oil can be recovered from the ground piscine or marine animal tissue or eggs. The omega-3 oil can be recovered from the liquid phase of the slurry once the liquid phase is separated from the solid particles of protein product. Omega-3 oils also can be recovered from the wash liquids or process filtrates. The solvents used during the process can be recovered from the process filtrates for subsequent reuse in the process. The amount of omega-3 oil in the slurry depends on the particular species of starting piscine or marine animal tissue. In some embodiments, the slurry can contain 25 wt % or less omega-3 oil.

Another advantage of the present invention can be to provide a system and method that improves the yield of recovered products.

Yet another advantage of the present invention can be to provide a system and method that improves shelf-life of the recovered products.

A further advantage of the present invention can be to provide a system and method that recycles the organic solvent and reduces VOC emissions into the atmosphere.

The present invention options can be considered a general recycling process for fish carcasses and related materials fit for human consumption that are otherwise discarded daily by facilities in the fish processing industry. The resultant recycling of the otherwise discarded materials to produce a high quality protein product affords a green and sustainable process that reduces the burden on the environment.

In one aspect of the present invention, an improved system and method for recovering products from animal tissue is described. Specifically, the technique involves combining animal tissue and organic solvent within a slurry tank in sufficient proportions to produce a mixture thereof. The mixture is agitated, heated (generally to a temperature no greater than 72° C., e.g., within the range of 25° C. to 72° C.) and separated using various separation options and then dried and milled to produce protein product powder. Preferably, the slurry tank is a single unitary structure outfitted with a mixing blade or agitator. The separation options can include continuous contacting belt or conveyor type filtration systems or centrifugation systems, such as vacuum belt filtration system, or an immersion extractor, or a percolation extractor, or a rotary drum filter, or a screw press, or a decanter/centrifuge, or combinations thereof. Also recovered is animal oil and water derived from the animal. In a preferred embodiment, the animal tissue is fish, and the recovered products include fish protein, fish oils and water derived from the fish. In an exemplary embodiment, the solid protein product is transferred to a grinding mill for further processing into a finely divided powder. In a yet another exemplary embodiment, a filtered, liquid portion of the mixture is filtered to separate fish oil from water. In a further embodiment, the portion of the mixture retained in the single unitary structure after filtration is combined with recycled organic solvent. The recycled organic solvent is recovered from the liquid portion of the mixture.

In another aspect of the present invention, an improved method for recovering products from animal tissue is provided. Specifically, the technique involves the use of a screw press system which has the effect of separating the water and omega-3 based oils from the fish tissue. The method involves dispensing raw fish and an organic solvent, such as isopropyl alcohol (IPA) or ethyl alcohol, in a ratio of at least 1 part volume of organic solvent to 1 part weight raw fish to a processing vessel, such as the aforementioned slurry tank, that is outfitted with a mixer or agitation system. The mixture is then stirred to yield a homogeneous slurry between a temperature of 25° C. to 72° C. The combined mixture of the organic solvent and raw fish are then transferred to the screw press where the liquid is separated from the raw fish. The resultant liquid filtrate derived from the screw press operation can be stored and subsequently processed for recovering the organic solvent. The pressed raw fish is returned to the slurry vessel and a second slurry cycle is performed. The screw press operation is optionally performed for at least two to three successive cycles.

In the methods and systems provided herein, various optional systems for recovering products from animal tissue can be used. Preferably, the animal tissue is fish. The systems include a screw press in combination with either a continuous belt filtration, immersion extraction system, percolating extraction system, or rotary drum filter, whereby an intermediate product wet-cake is discharged into a drying unit. Animal tissue feedstock and organic solvent are independently, or collectively, transferred onto either of these optional processing devices. These filtration units allow the raw material feedstock to be washed with solvent to yield a purified intermediate product wet-cake. The filtration system options include subsystems for recycling and removing filtrate, as well as an output for removing solid product.

Provided herein are systems for recovering a protein product powder and purified omega-3 oils from an animal tissue. The systems include a grinding unit, a slurry preparation unit, a dewatering device, a closed system product separation system for separating the slurry into a liquid phase and a solid phase, the separation system including a continuous conveyance filtration system selected from among a belt filtration system, a rotary drum filter, an immersion extractor, a percolator extractor, and a screw press, or a centrifugation system, such as a decanter centrifuge, or any combination thereof, and a solvent/liquid recovery (SLR) system that includes a liquid phase processing unit, a separation unit that separates the liquid phase into recovered organic solvent, water and an omega-3 oil, and a recovered organic solvent storage tank. The system can include a drying unit. The system can include a milling unit.

In some embodiments, the system is manual. In some embodiments, the system is automated. The system can be automated by using a programmable logic controller (PLC) and a customizable recipe-driven software architecture (e.g., depending on the fish species or final desired product characteristics, where the PLC is the automated programmable device for controlling the process automatically without the need for manual intervention.

The separation unit of the system can include a distillation unit or a centrifugation unit or a combination thereof. The distillation unit can include single column or a plurality of distillation columns. The distillation unit can include a thin film evaporator or a wiped film evaporator. The system can include a process control system that analyzes the overhead vapor pressure and the temperature of the distillation unit.

The system can include a liquid phase processing unit that contains an adsorber system or an activated carbon filtration system or both. The system can include an analyzer system. The analyzer system can analyze the adsorber effluent stream for detection free amines or small chain hydrocarbon materials. If these materials are detected, the analyzer system can make adjustments in order to minimize or eliminate free amines or small chain hydrocarbon materials from the protein product.

The slurry preparation unit of the system can include a preparation tank for receiving and mixing ground animal tissue from a grinding unit with a solvent to form a slurry. The system can include a closed system recycling solvent loop that transports recovered organic solvent from the recovered organic solvent storage tank to slurry preparation unit. The system can include a volatile organic carbon recycling system that captures process emissions of the organic solvent to form a condensed liquid solvent from the filtration process via condensation and transports the condensed liquid solvent to the closed loop recycler. The system also can include a variable frequency drive (VFD) to modulate the speed of the conveyance filtration system or the centrifugation system.

Also provided are methods for recovering protein product powder and omega-3 oil from an animal tissue. The methods include mixing the animal tissue with an organic solvent in a preparation tank; comminuting the animal tissue with the organic solvent to produce a slurry; separating the slurry into a liquid phase and a solid phase using a separation system selected from among a belt filtration system, a rotary drum filtration system, an immersion extraction system, a percolation extraction system, a screw press filtration system, a centrifugation system, such as a decanter centrifuge, and any combination thereof; recovering the liquid phase and separating it into a recovered organic solvent portion and an omega-3 oil portion; recovering the solid phase and drying it to yield a protein wetcake; and milling the protein wetcake to yield protein product powder. In the methods, the animal tissue can include raw fish that is processed through a dewatering device to remove excess water. The dewatering device also can be configured to mix dewatered slurry with the organic solvent to form a processed slurry. In the methods, the organic solvent mixed with the animal tissue or with the dewatered slurry can include an alcohol, an aliphatic hydrocarbon, an ester, water or any combination thereof.

In the methods provided, the vapor produced during drying the solid phase can be captured and condensed into a liquid and organic solvent can be separated from the liquid and recovered, e.g., for reuse in the system. The organic solvent mixed with the animal tissue or with the dewatered slurry can include at least a portion of the recovered organic solvent derived from the condensed vapor derived from the drying step of an earlier processed slurry. In some embodiments, dried protein product is milled into a powder. In some embodiments, a jet mill reduces the particles size of the dry protein product into a powder.

In the methods provided herein, the yield of protein can be in the range of from about 10% to 20%, based on the total weight of the starting animal tissue. In some applications, the yield of protein can be about 18 wt % or greater based on the total weight of the starting animal tissue. The amount of protein recovered can depend on the starting material, e.g., the type of species or blend of species used, and the composition of the starting material, e.g., the total water/oil/protein content of the starting material. The systems and methods provided herein can be used to produce a protein product powder. The protein product powder can have a moisture content of less than about 10 wt %. In some applications, the protein product powder can have a moisture content of less than about 1 wt %, or less than about 0.5%. In some applications, the protein product powder can have a moisture content in the range from about 0.15% to about 1%. The protein product powder can have an amount of residual organic solvent of less than about 0.5 wt % h, or about 250 ppm or less. The amount of protein in the protein product powder can be at least about 50 wt % protein, or can be greater than about 80 wt %, or greater than about 90 wt %, or greater than 95 wt %. In some applications, the amount of protein in the protein product powder can be between about 90 wt % and 98 wt %, or from about 90 wt % to about 96 wt %. In some applications, the amount of protein in the protein product powder is in the range of from about 45 wt % to about 96 wt %. The protein product powder has a crude fat content of less than about 1.5 wt % and a cholesterol content of less than about 0.1 wt %. In some applications, protein product powder can have a crude fat content of less than about 1 wt %, or less than about 0.5 wt %. In some applications, protein product powder can have a crude fat content from about 0.15 wt % to about 0.5 wt %.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed. Reference will now be made in detail to embodiments of the present invention, examples of which are illustrated in the accompanying drawings.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION

Definitions

Figure 1:
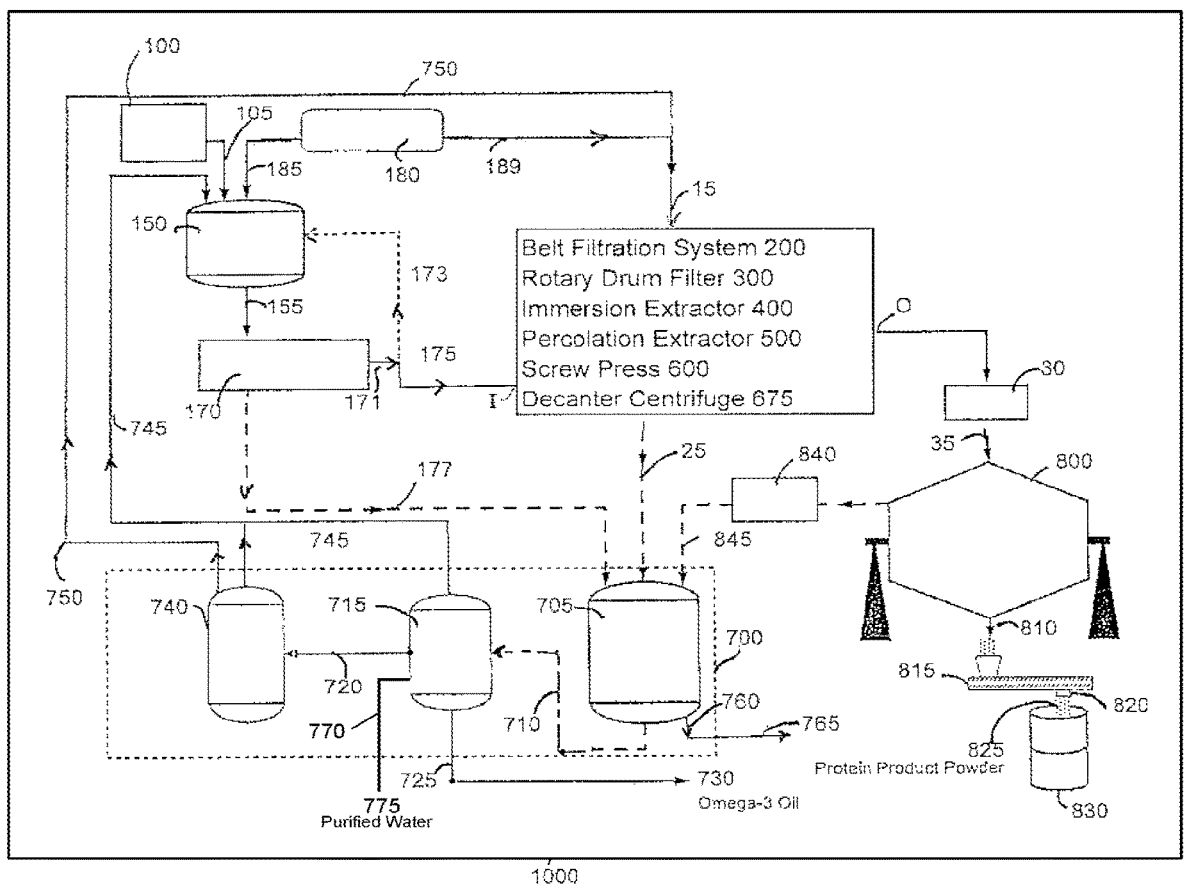
FIG. 1 is an illustration of the product recovery system provided herein showing the various protein isolation options in accordance with exemplary embodiments of the present invention. As shown, the product recovery system 1000 includes a grinding unit 100, a slurry preparation tank 150, a dewatering device 170, a product separation system 10 that can include one or more of a belt filtration system, a rotary drum filter, an immersion extractor, a percolation extractor, a screw press, a decanter centrifuge. or any combination thereof. The product recovery system 1000 also includes a solvent/liquid recovery (SLR) system 700 for recovering the solvent for reuse and for processing the recovered omega-3 oil. The SLR system 700 includes a liquid phase processing unit 705 and a separation unit 715 and optionally a recovered solvent tank 740. The product recovery system 1000 also includes a solvent supply tank 180, discharge stage 30, a dryer unit 800, a vapor condenser 805 and a milling unit 815.

Unless defined otherwise, all technical and scientific terms used herein have the same meaning as is commonly understood by one of skill in the art to which the inventions belong.

All patents, patent applications, published applications and publications, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

As used herein, "impurities" refers to any substance other than animal tissue, protein, oils, solvent, and water. Such impurities can include, e.g., oxidation byproducts, free amines, such as dimethyl, trimethyl, and homologues of similarly aminated species, cholesterol, and volatile odoriferous compounds.

As used herein, "low-moisture wetcake" refers to a wetcake containing a liquid in an amount in excess of 2 weight percent.

As used herein, "vacuum belt filter" refers to a device that uses a pressure differential created by a vacuum source cross a conveyor belt filter to facilitate solid/liquid separation.

As used herein, "rotary pressure/vacuum drum filter" refers to a device that uses a pressure or vacuum differential across a rotating drum filter to facilitate solid/liquid separation.

As used herein, a "continuous feed immersion type solvent extractor" refers to a device that includes serially connected cascading pools for separating a liquid and a solid where the solids being processed are soaked in the solvent as the material is conveyed through the device.

As used herein, a "continuous feed percolation type solvent extractor" refers to a device for separating a liquid and a solid that includes a mechanical conveyance system and a solvent application system where the solvent is washed through the solids being processed. The solvent can be applied from the bottom or from the top of the solids.

As used herein, a "decanter centrifuge" refers to centrifugation separation device that separates solids from liquids using centrifugal forces. Generally, when the mix of solids and liquids is subject to centrifugal forces in the device, the denser solids are pressed outward, generally against a rotating bowl wall, with the lighter liquid layer in a concentric inner layer, and dam plates can be used to direct the flow of the fluid, resulting in the separation of the solids from the liquid in a single continuous process.

As used here, the singular forms "a," "an" and "the" include plural referents unless the context clearly dictates otherwise.

As used herein, ranges and amounts can be expressed as "about" a particular value or range. "About" also includes the exact amount. Hence "about 5 percent" means "about 5 percent" and also "5 percent." "About" means within typical experimental error for the application or purpose intended.

As used herein, "optional" or "optionally" means that the subsequently described element, event or circumstance does or does not occur, and that the description includes instances where the element, event or circumstance occurs and instances where it does not. For example, an optional component in a system means that the component may be present or may not be present in the system.

As used herein, "animal tissue" is material that can contain the complete animal components inclusive of tissue, bones, and scales.

In the examples, and throughout this disclosure, all parts and percentages are by weight (wt %) and all temperatures are in ° C., unless otherwise indicated.

As used herein, the phrase "based on the weight of the composition" with reference to % refers to wt % (mass % or (wt/wt) %).

As used herein, "natural omega-3 oil" refers to omega-3 oil that is not chemically modified and that is suitable for human consumption.

As used herein, "modular" means that the components of the system are designed with standardized dimensions or inter-connections, to allow for easy assembly an disassembly and flexible arrangement and use.

Product Recovery Systems and Methods

The present invention describes several systems and processes for improving the efficiency of recovering products from animal tissue. Also described are systems and processes for improving throughput, especially yield of solid protein, based upon the initial feed of animal tissue. Also provided are systems and processes for reducing the emission of volatile organic compound (VOC) gases into the atmosphere during the processing of animal tissue.

Generally, condensing plural pieces of third-party manufacturing equipment modified to fit and accommodate the methods described herein to output materials fit for human consumption, and configured into a single modular unitary structure has been shown by the inventors to reduce downtime caused by material flow obstructions occurring at multiple locations in the system. Namely, material flow obstructions occur most frequently at inputs and outputs of manufacturing equipment. Material flow obstructions also occur within conduits connecting different pieces of manufacturing equipment. According to the inventors, processing animal tissue feedstock using a continuous belt filter or similar mentioned solvent extraction systems to recover a wet cake including solid protein significantly improves (i.e. reduces) downtime attributed to maintenance and repair. In addition, the current systems and methods can be operated manually or can be automated processes. The systems and methods are more energy efficient and require less manpower than a system that includes multiple unit operations. Another advantage directly attributed to employing the above-mentioned system is the ability for increased product throughput in addition to a reduction in capital and operational costs associated with procuring and maintaining multiple pieces of equipment required to produce the same quantities of final product. Yet another advantage realized by the inventors is an improvement in yield of solid protein and shelf-life, derived from the wet cake by employing the system and method described herein.

The systems and processes provided herein will be discussed in greater detail below in view of the exemplary, non-limiting embodiments of the present invention. Each of the embodiments discussed hereinafter, unless expressly noted otherwise, are combinable and envisaged within the scope of the present invention. It is also understood that the embodiments, while preferred, are exemplary, and those of ordinary skilled in the art will understand certain modifications to the embodiments are possible without departing from the spirit of the invention.

Systems

FIG. 1 is a process overview illustrating an exemplary embodiment of a protein recovery system provided herein. As shown in FIG. 1, the recovery system 1000 includes a grinding unit 100 that can receive an animal tissue feedstock, such as raw fish, for introducing animal tissue. The animal tissue feedstock can be contained within a storage tank before it is transferred to grinding unit 100. The storage tank can be temperature controlled. Alternatively, the animal tissue can be housed in a cold room and conveyed downstream for processing either manually by technicians, or by any combination of automatic machinery including but not limited to screw conveyers, conduits/tubes, pumps, blowers, etc. In an exemplary embodiment, stainless steel piping can be employed throughout the system. In another exemplary embodiment, a pump constructed of stainless steel can be used to assist with transferring animal tissue to the grinding unit 100.

The recovery system 1000 also includes a slurry preparation tank 150 into which the ground animal tissue is discharged via line 105. The ground animal tissue is mixed with a solvent in the slurry preparation tank to form a crude slurry. The recovery system 1000 includes a solvent storage tank 180 for providing an organic solvent feed to slurry preparation tank 150 as well as a recycled solvent feed line 745 that can be used to direct recovered solvent into slurry preparation tank 150. Any organic solvent, such as ethanol or isopropyl alcohol (IPA) or ethyl alcohol or combinations thereof, can be used as a permissible organic solvent. The storage tank 180 can have a flat bottom or a curved bottom and generally is closed to the environment (e.g., includes a closed or closable top). The storage tank 180 can also include a level transmitter for monitoring solvent inventory. The storage tank 180 can include nozzles that directly or indirectly communicate with an inlet of nitrogen or similarly inert gas for introducing an inert gas into the storage tank 180. The storage tank 180 also can include a conservation valve, butterfly valve, and/or diaphragm valve. The organic solvent can be delivered downstream by any combination of equipment including but not limited to piping, hoses, pumps, blowers, valves or the like. In some embodiments, a pump is present to deliver the solvent to other components of recovery system 1000. When present, the pump can be stainless steel and centrifugal. Piping and/or tubing can be employed as necessary for interconnecting the different components of recovery system 1000.

The present invention involves a highly scalable process and is capable of yielding protein powder and omega-3 oils ranging from lower to higher quantities. The process is highly modular and therefore also reconfigurable in that parallel trains of similar or combinations of the optional systems can be implemented for concurrent production requirements. The system can be operated manually or can be automated. In some embodiments, at least one process of the system is automated.

The process can be configured to be highly modular, where the system includes a plurality of modules, each module comprising a piece of equipment. The modules can be designed to be movable, and the modules can be designed to allow connection to other modules. The connection can be direct, or a connecting unit can connect different modules together. The modules can be adaptable for a plurality of manufacturing steps or processes. Very little time is required to reconfigure the system, such as changing one module to perform a different step or process, and/or including a plurality of the same modules, e.g., to extend a process line, or extend a treatment step. Because of the modular nature of the system, it is relatively inexpensive to expand the system, or to acquire additional modules. It also is easy to incorporate new or additional modules into the system.

In some applications, all components can be contained in one module. In some applications, individual components of the system can be contained in separate modules. For example, individual modules can include a grinding module, or a slurry preparation module, or a dewatering module, or a concentrator module (e.g., containing a belt filtration system, or rotary drum filter, or immersion extractor, or percolation extractor, or screw press, or decanter centrifuge), or a drying module, or a milling module, or a packaging module, or a solvent/liquid recovery module. Some systems can contain two or more components in a single module. Some systems can include multiples of individual modules. For example, several drying modules can be configured in series in order to extend the path the product takes through drying equipment contained in the drying modules. As another example, a concentration module containing a screw press can be attached to a concentration module containing a belt filtration system.

Each module can be separately movable from another module. modules can take on a plurality of forms, sizes, shapes, and/or configurations. Any suitable number of modules can be provided in a particular modular manufacturing system depending on a particular manufacturing need and/or manufacturing facility space limitation or requirement. The modules can form a system that is used in a marine environment. In such configurations, the modules can include fasteners that can be attached to a frame connected to the deck or a wall of the ship, or each module can separately be connected to a deck or wall of a ship. The modules can form a system that is land-based. In such configurations, the modules can be attached to a frame affixed to the ground, or each module separately can be attached to a floor or wall. The equipment within each module is easily separated from the equipment contained in another module. The modules allow for easy change-over, such as by modifying, moving, adding to, and/or reconfiguring equipment mounted to portion of the modules and/or by simply replacing a module, or replacing the equipment within a module. For example, a piece of equipment in a module can be disconnected from a piece of equipment in another module and the module can be replaced with another module. In some configurations, the module can be configured to separately accommodate two or more pieces of equipment, and the system can be modified by unattaching a piece of equipment in the module, removing the piece of equipment from the module, and placing a different piece of equipment in the module.

The equipment can be held to the portions of the modules using bolts, pins, rods, quick-connect mechanisms, and/or other attachment devices. Each module can include one or more mounting and alignment portions for connecting to, operably engaging with, and/or aligning with neighboring modules, standard forklift pickup channels, chains, and/or hooks, and/or built in and/or attachable conveyors. Each module can include integrated power and communication systems that can interact with other modules. Each module can include conduits for wires or cables, and can include conduits for utilities such as water, compressed air, heating, cooling, and vacuum systems. Each module can enclosure doors, shields, or guards or combinations thereof to at least inhibit dust or dirt infiltration and to reduce the noise produced by the module.

Of particular importance, the recovery system can include one or a combination of six different separation system options, namely a belt filtration system, a rotary drum filter, an immersion extraction system, a percolation extraction system, a screw press system, and a decanter centrifuge system. Any one or combination of these systems can be included in the product separation system 10 in FIG. 1 and used to separate the protein product from the omega-3 oil. Some of these units can include a filter for separating solids from heavy liquids. Some of these systems also can include one or more filtrate pump devices that can recycle the process filtrate back into the process to allow more efficient washing of the protein product wet cake. Preferably, these systems can be constructed of stainless steel or solvent resistant polymeric material, such as polypropylene, and are of a sanitary design.

The overall protein recovery system 1000 illustrated in FIG. 1 also includes a product drying system 805 that can be further followed by a milling unit 815 such as micronizer or milling device. A solvent/liquid recycle (SLR) system 700 is also present, as illustrated in FIG. 1. The SLR system 700 includes a processing unit 705 and separation unit 715, which can include adsorber and distillation units. The SLR system 700 can include one or more filtrate recovery tanks (not shown in FIG. 1) for storage or containing hold up volumes. Preferably, the filtrate recovery tanks are made of stainless steel. The filtrate tanks can include one or more inlet nozzles that directly or indirectly communicate with an inlet for feeding nitrogen or other inert gas into the recovery tank. The nitrogen or inert gas forms an inert gas blanket that maintains a reduced level of oxygen in the organic vapor space to eliminate the potential for explosion or oxidation of products. The SLR system 700 is used to process the spent filtrates by recovery of the organic solvent using an adsorber bed contained within processing unit 705, followed by a distillation system, which is a part of separation unit 715.

The distillation system that is a part of separation unit 715 can be a simple batch type still equipped with an overhead condenser and distillate receiver. The distillation unit also can be a wiped or thin film evaporator unit. A thin film or wiped film evaporator (WFE) can be used for concentrating, separating, refining, decolorizing and deodorizing liquid streams containing solvents. The liquid streams are separated into distillate and residue components. In a WFE system, the process filtrate enters through the inlet of the WFE and is dispersed across a distributor plate into an internal heating wall. Rotating wipers within the body of the WFE spread the liquid to a uniform thin film. Vaporized liquid condenses as distillate. The residue component is collected in a separate vessel. The resultant distillate includes the recovered solvent for recycling back into the process, such as via line 745 or line 750 or both. The distillation residue will contain a high concentration of omega-3 oil that can exit separation unit 715 via line 725, and can be optionally processed further using molecular distillation technologies or their equivalent. The distillation residue can be optionally processed using chemical reaction processing, such as transesterification.

In some embodiments, the SLR system 700 can include a recovered solvent tank 740. Recovered solvent from separation unit 715 can be transferred to recovered solvent tank 740 via line 720. The recovered solvent tank 740 can have a flat bottom or a curved bottom and generally is closed to the environment (e.g., includes a closed or closable top). The recovered solvent tank 740 can also include a level transmitter for monitoring solvent inventory. The recovered solvent tank 740 can include nozzles that directly or indirectly communicate with an inlet of nitrogen or similarly inert gas for introducing an inert gas into the recovered solvent tank 740. The recovered solvent tank 740 also can include a conservation valve, butterfly valve, and/or diaphragm valve. The organic solvent can be delivered downstream by any combination of equipment including but not limited to piping, hoses, pumps, blowers, valves or the like. In some embodiments, a pump is present to deliver the solvent to other components of recovery system 1000. When present, the pump can be stainless steel and centrifugal. Piping and/or tubing can be employed as necessary for interconnecting the different components of recovery system 1000.

Slurry Preparation

Still referencing FIG. 1, generation of a crude slurry is accomplished by first producing a finely ground animal tissue from the starting material. In some embodiments, the finely ground animal tissue is prepared using an extraction system that includes the grinding unit 100 that comminutes the starting material into small pieces in the presence of an extraction solvent to produce the crude slurry. The starting material can contain animal tissue containing a bulk protein mass containing polypeptides and a mixture of oils, such omega-3 type oils. Suitable examples of the starting material include, but are not limited to, animal tissue material derived from flesh or eggs from anchovies, arctic char, mackerel, sablefish, herrings, sardines, salmon, hake (cod family), halibut, carp, trout, oysters, krill, squid, shrimp and cuttlefish, and as an optional starting raw material, dried fishmeal or dried fish, or any combinations thereof. In some embodiments, the starting material comprises piscine eggs or tissue or parts thereof that contain about 65 wt % to about 75 wt % water, about 15 wt % to about 25 wt % protein, about 4 wt % to about 8 wt % oil, and about 1 wt % to about 5 wt % other material, such as carbohydrates or ash-producing material, e.g., bones.

The ground animal tissue can be prepared by dispensing whole raw fish and/or raw fish parts into the grinding unit 100. The resultant ground material can contain the complete animal components inclusive of tissue, bones, and scales. In some embodiments of the methods and systems provided herein, the ground material can include water from the starting material, and amounts of omega-3 oil from the ground starting material, and optionally can include extraction solvent, which can include water, which can be added to the starting material during the grinding process. The ground material contains a solid phase and a liquid phase and can contain impurities.

The starting material is subjected to a grinding operation in grinding unit 100. Grinding unit 100 can include any type of equipment that can reduce the particle size of the starting material, such as a pulverizer, homogenizer, high speed blender, rotor-stator mixer or any combination thereof. The grinding unit 100 includes a vessel equipped with an overhead mixer or agitator assembly that is used to stir the mixture within the vessel. The vessel has an inlet feed nozzle for dispensing solvent and a charging port for dispensing the raw animal tissue. The vessel can contain a valve, such as a bottom valve, for discharging the ground material slurry. The grinding of the starting material reduces the particle size of the raw fish to about 6300 μm (0.25 inches) or less. In some embodiments, the grinding process is continued until the average particle size of the ground animal tissue, e.g., ground raw fish, is about 5000 μm or less, or about 4000 μm or less. No heat is applied to the starting material in the grinding tank other than any frictional heating that could occur due to the grinding and/or mixing process. The grinding process is exclusively mechanical, and the starting material is not treated with an acid or a protease prior to grinding. A solvent can be added to the animal tissue before or during the grinding process. In some embodiments, the temperature of the ground material is 25° C. or less after its production. The resulting ground material is used to make a crude slurry.

A crude slurry is prepared in slurry preparation tank 150 and can contain a liquid phase in an amount in the range of from about 40 wt % to 99 wt % based on the weight of the slurry. The liquid phase of the slurry can include water or an organic solvent or combinations thereof. The crude slurry also can contain particles of piscine tissue or marine animal tissue or fish meal or dried fish or combinations thereof. The particles of piscine tissue or marine animal tissue or fish meal or dried fish in the slurry can be present in an amount in the range of from about 1 wt % to about 99 wt %, or from about 40 wt % to about 99 wt % based on the weight of the slurry. Depending on the starting material, the slurry also can include particles of bone or carbohydrate-containing particles or combinations thereof.

The crude slurry can be prepared by mixing the ground starting material, such as ground piscine tissue or parts thereof, or marine animal tissue or parts thereof, or dehydrated fishmeal, or commodity dried fish, or combinations thereof, with an extraction solvent in slurry preparation tank 150 to form a mixture. The extraction solvent can include water or an organic solvent or combinations thereof. In some embodiments, the extraction solvent includes an alcohol, an aliphatic hydrocarbon, an ester, water or any combination thereof. The ground material can be introduced into the slurry preparation tank 150 via line 105. An organic solvent can be introduced into slurry preparation tank 150. The organic solvent can be fresh virgin solvent from storage tank 180, which can be fed into slurry preparation tank 150 via solvent line 185. The organic solvent also can be solvent recovered from the process using the SLR system 700, which includes liquid phase processing unit 705 and separation unit 715. The separation unit 715 can separate the liquid into water and organic solvent and omega-3 oils. The recovered solvent from the SLR system 700 can be fed into slurry preparation tank 150 via feed line 745. The SLR system 700 can include a closed system recycling solvent loop that transports recovered organic solvent from the recovered organic solvent storage tank 740 to the slurry preparation tank 150 or to the product wash inlet 15 or both. The systems provided herein also can include a volatile organic carbon recycling system that captures process emissions of organic solvent and condenses them into liquid form and transports the condensed liquid solvent to the closed system recycling solvent loop.

A combination of fresh virgin solvent and recovered solvent can be used in the slurry preparation tank 150. In some embodiments, separation unit 715 includes a distillation system. The separation unit 715 can separate the $ In the slurry preparation tank 150, the ground material is mixed with an organic solvent, and the material is agitated to achieve a homogeneous mixture and thereby produce the crude slurry. In some embodiments, the crude slurry preferably comprises a 1:1 ratio (volume of organic solvent to weight of animal tissue) mixture of ground raw animal tissue and organic solvent.

The slurry preparation tank 150 can include a primary agitator assembly and a temperature control system for modulating the temperature of the slurry during preparation. The temperature control system can include a heating source for providing thermal energy to the slurry preparation tank 150 in order to adjust the temperature of the slurry mixture in the slurry tank. The primary agitator assembly can include a rotating mixing shaft with blades, where the mixing blades can be rotated by an overhead motor to achieve uniform mixing in the tank. This can ensure uniform mixing and heating, thus eliminating localized thermally heated zones in the tank that are in contact with the animal tissue and organic solvent mixture, particularly that portion of the mixture in proximity of the heated walls or bottom of the slurry preparation vessel. Such localized contact with thermally hot zones can induce decomposition and/or denaturing of the protein. In ensuring a thermally stable and adequately mixed environment in the slurry tank, protein conforming to the product specification will be recovered, specifically with 85% or higher protein content, as characterized by the resultant amino acid profile conducted through final product analysis.

The heating source can include a jacket encompassing at least a portion of the slurry preparation tank 150 through which a thermal heating fluid, such as steam or heated oil, can be circulated or pumped; or an immersion heater that can be inserted directly into the slurry; or electrical heating elements that are in thermal communication with at least a portion of the tank; or any combination thereof. The slurry tank also can include a jacketing and insulation system to permit cooling of the tank. In some embodiment, the slurry tank includes a jacketing and insulation system that can heat and cool the tank. The slurry tank also can include a variable control system that includes a temperature sensor that is immersed into the contents of the tank and that measures the actual temperature of the mixture. The slurry tank also can include a temperature feedback controller to regulate the amount of thermal energy provided to the tank to adjust the temperature of the slurry. In some embodiments, the temperature feedback controller regulates the amount of steam, thermal heating fluid, or electrical wattage that is provided to the heating source used to heat the contents of the tank. For example, the temperature controller can modulate a control valve, or wattage regulator, or a combination thereof, to control the steam, thermal heating fluid, or amperes available to the heating source. Processing in the slurry preparation tank, and in particular, the heating process, can be done at a controlled temperature using a variable control system that includes a temperature sensor that is immersed into the contents of the tank and that measures the actual temperature of the mixture. A corresponding temperature feedback controller measures the process temperature and regulates the amount of steam, thermal heating fluid, or electrical wattage that is used to heat the contents of the tank. The temperature controller can modulate a control valve, or wattage regulator, to control the steam, thermal heating fluid, or amperes to achieve a specified temperature setpoint, such as 70° C. to prevent the decomposition and/or denaturation of the protein material associated with the raw fish or fishmeal. By preventing decomposition and/or denaturation of the protein material, the amount of protein recovered generally can be from about 40 wt % to about 99 wt %, or between 50 wt % and 92 wt*o 8 wt %, or can be greater than 60 wt %, 70 wt %, 80 wt % or 90 wt %, depending on the species, mix of species or the composition of the original raw starting material.

Water Reduction

The initial animal tissue may contain a water content as high as 75-80%, which can interfere with the efficient processing of the material. The crude slurry prepared in slurry preparation tank 150 thus can contain amounts of water that can interfere with the efficient processing. Therefore, in some embodiments, the crude slurry can be transferred to a dewatering device 170 where the crude slurry is processed to separate liquid from the ground solid animal tissue. Any device or system for removing at least a portion of the liquid from the crude slurry can be used. For example, the dewatering device 170 can include a screw press, or a plate press, or a centrifuge, or a combination thereof for mechanically removing at least a portion of the liquid from the crude slurry prior to further processing. Dewatering devices are known in the art (e.g., see U.S. Pat. Nos. 4,266,473; 4,441,797; 4,685,899; 5,958,233; 6,634,508; and International Patent Application Publication WO 1997/040941).

In some embodiments, the dewatering device 170 includes a screw press. The compression action of the screw press on the crude slurry can displace some of the liquid from the slurry, including water that was initially contained in the raw starting material. The press liquid from the dewatering device 170 can exit the dewatering device 170 via line 177 and be routed to liquid phase processing unit 705. The recovered dewatered material can be routed to inlet I of product separation system 10 via line 175 for further processing, or can be routed back to dewatering device 170 via line 173 for repeated dewatering. The dewatering operation in dewatering device 170 can be repeated as necessary to achieve the removal of the desired amount of liquid. In some embodiments, the dewatering operation of dewatering device 170 results in the removal of at least 50%, or at least 75%, or at least 80% of the water that was initially contained with the raw animal tissue.

In some embodiments, when the dewatering device 170 includes a screw press, the speed of the conveyance of material through the screw press can be controlled using a variable frequency drive (VFD) technology coordinated with controlling the screw press. A VFD is a motor controlling device that can operate the motor at various speeds. By using a VFD, the amount of material produced by the screw press can be controlled at various rates.

In some embodiments, the dewatering device 170 is or can include a decanter centrifuge. Decanter centrifuges are well known in the art (e.g., see U.S. Pat. Nos. 4,298,162; 4,566,873; 4,731,182; 4,790,806; 4,825,541; 5,047,004; 5,178,602; 5,257,968; 5,261,869; 5,267,936; 5,342,279; 7,156,801; 8,152,708; 8,968,169; and 9,028,387; and U.S. Pat. Appl. Pub. Nos. US2011/0160031 and US2011/0315621. These decanter centrifuges are commercially available. Exemplary decanter centrifuges suitable for use in the dewatering device 170 are manufactured by Alfa-Laval Inc. (Richmond, VA) and GEA Mechanical Equipment, Inc. (Northvale, NJ). The decanter centrifuge generally includes a rotating cylinder with an internal screw. The cylinder and screw are rotated at high speeds. The crude slurry to be dewatered is fed into the centrifuge via a central inlet pipe. Rotational forces act upon the crude slurry, forcing it towards the periphery of the cylinder. Particles of the ground raw animal tissue are caused to separate out against the cylinder into a sediment by the centrifugal forces established by the centrifuge. The screw of the centrifuge moves the resultant sediment toward an outlet. In some embodiments, the dewatering device 170 can be configured so that the slurry passes through it without a significant change in water or solvent content. In some embodiments, the slurry from slurry tank 150 does not need to be dewatered. In such embodiments, the slurry can be transported via appropriate pipes or tubing (not shown in FIG. 1) directly to inlet I of the product separation system 10.

After passing through dewatering device 170, the resulting processed slurry can exit the dewatering device 170 via outlet 171 and can be transferred to any one of the six aforementioned separation systems of product separation system 10 via slurry outlet 175 and inlet I of product separation system 10 for further processing. The processed slurry can be a homogeneous mixture of animal tissue and organic solvent, and can contain residual water. The processes slurry also can exit the dewatering device 170 via outlet 171 and be diverted back to the slurry preparation tank 150 via line 173 for further processing, e.g., to add solvent from lines 185 or 745 or both to modulate the viscosity or fluidity of the solvent, or for additional dewatering.

In some embodiments, the processed slurry can have a temperature of at least about 25° C. immediately upon being introduced into the product separation system 10 section of product recovery system 1000. In some embodiments, the processed slurry can have a temperature of from about 25° C. to about 72° C. immediately upon being introduced into product processing system 10.

At least one section of the product separation system 10 of the product recovery system 1000 provided herein can separate the processed slurry into a liquid phase and a solid phase. The liquid phase can include extraction solvent, residual water that was contained within the starting material, oxidation byproducts, and omega-3 oil or any combination thereof. In some embodiments, the extraction solvent can include water, an aliphatic hydrocarbon, such as hexane, an alcohol, or an ester or any combination thereof. The liquid phase can contain an extraction solvent in an amount of at least about 50 wt %. In some embodiments, the liquid phase can include an omega-3 oil. The amount of omega-3 oil present will depend on the starting animal tissue. In some embodiments, the omega-3 oil is present in an amount of less than about 20 wt %.

The product separation system 10 separates the processed slurry into a filtrate and a solid phase wetcake. The solid phase wetcake contains the recovered protein product. The solid phase wetcake containing the recovered protein product exits product separation system 10 through outlet O. In some embodiments, the solid phase wetcake containing the recovered protein product can be collected on a discharge stage 30 prior to moving to further processing stations, such as dryer unit 800 via line 35.

The solid phase wetcake containing the recovered protein product can be transported to dryer unit 800 via line 35 for additional drying. The type and configuration of the dryer unit 800 can be selected to optimize the amount of moisture removed from the wetcake without negatively impact protein product quality. For example, forced air, direct infrared (IR), indirect IR or convection ovens can be used to directly or indirectly dry the wetcake. Additional drying units can include a tray drying system, rotary cone vacuum dryer, fluid bed dryer or spray drying unit. In some embodiments, dryer unit 800 can include a vacuum system. In some embodiments, the wetcake is dried to a moisture content of 10 wt % or less, or 5 wt % or less, or 1 wt % or less, and a residual organic solvent content of about 1 wt % or less, or less than 0.5 wt %, or less than about 500 ppm, under full vacuum at a temperature of 100° C. or less, such as 80° C. or less, resulting in a dried product The dried product is removed from the dryer unit 800 at 810 and subjected to a particle size reduction operation using a milling unit 815. Milling unit 815 can include any particle size reducing device suitable for production of particles of a target particle size. Exemplary particle size reducing devices include primary impact crushers, secondary crushers, cage mills, ball mills, hammer mills, jet mills, micronizing devices, pulverizers and grinders, including ultrafine grinders. In some embodiments, the milling unit 815 includes a micronizing device or jet mill device. The milled product 825 is a powdered protein product, which exits milling unit 815 via outlet 820 and collected into a packaging device 830. Exemplary packaging devices include a sealable container, a case, a box, an intermediate bulk container or tote, a drum, a bag, a barrel, a bag-in-bag container, and a bag-in-box container.

The vapor produced in dryer unit 800 can be removed via a vacuum line. A vapor condenser 840 is attached to the vacuum line and operates to condense the vapor produced by the dryer unit 800 into a liquid for recycling. The condensed liquid produced in vapor condenser 840 can be routed to processing unit 705 via line 845 for further processing and recycling.

The filtrate that exits the product separation system 10 can be directed to processing unit 705 via line 25 for further processing to yield a purified filtrate, which can be directed to separation unit 715 via line 710 to separate the purified filtrate into an oil fraction and a solvent fraction. Processing unit 705 can include, e.g., adsorber and carbon filtration units. The adsorber can be a fixed, packed bed column comprising resin particles or beads. The particular resin beads selected will have an affinity for free amines and miscellaneous undesired hydrocarbons present in the filtrate. The filtrate is transferred through the adsorber bed, and the resultant stream which exits the adsorber will be a purified filtrate. Filtered waste material can exit processing unit 705 at waste exit 760 and removed via line 765. The adsorption process occurs at ambient conditions. The carbon filtration unit is also a fixed bed operation and is used as polishing step following the adsorption process. Purified filtrate then is directed to separation unit 715 via line 710 for separating the oil fraction from the solvent fraction.

In some embodiments, separation is accomplished using centrifugation. In some embodiments, separation is accomplished using distillation. In some embodiments, separation is accomplished using a combination of centrifugation and distillation. In some embodiments, the separation unit 715 can include a distillation system. The distillation system can be a simple batch type still equipped with an overhead condenser and distillate receiver. The distillation system can also be or include a wiped or thin film evaporator unit. The separation unit 715 can separate the purified filtrate into recovered solvent, purified water 775, and omega-3 oils 730. Referring to FIG. 1, the omega-3 oil 730 can exit separation unit 715 via recovered oil transfer line 725. The purified water 775 can exit separation unit 715 via purified water outlet 770. The recovered solvent can be directed to recovered solvent tank 740 via recovered solvent transfer line 720 or directed to the slurry preparation tank 150 via recovered solvent line 745. The distillation residue can contain a high concentration of omega-3 oil that can be optionally processed further using molecular distillation technologies or chemical processing via transesterification. The recovered solvent can be reused in the system, such as by directing the recovered solvent to the slurry preparation tank 150 via slurry tank feed line 745. The recovered solvent also can be directed via line 720 to recovered solvent tank 740 where it can be stored for reuse in the system 1000.

In some embodiments of the methods and systems provided herein, the product separation system 10 can separate the solid phase and the liquid phase of the processed slurry by depositing the processed slurry on a surface of a filter, where the solid particles are retained on the surface of the filter forming a wetcake, and at least a portion of the liquid phase of the processed slurry passes through the filter. In some embodiments, the product separation system 10 can include, e.g., a vacuum belt filter, an immersion extractor, a percolation extractor, a rotary pressure drum filter, a screw press, a decanter centrifuge, or a combination of any two or more of these. In some embodiments, the product separation system 10 is a closed system, preventing release of solvent into the environment and allowing recovery of the solvent.

Belt Filtration

Figure 2:
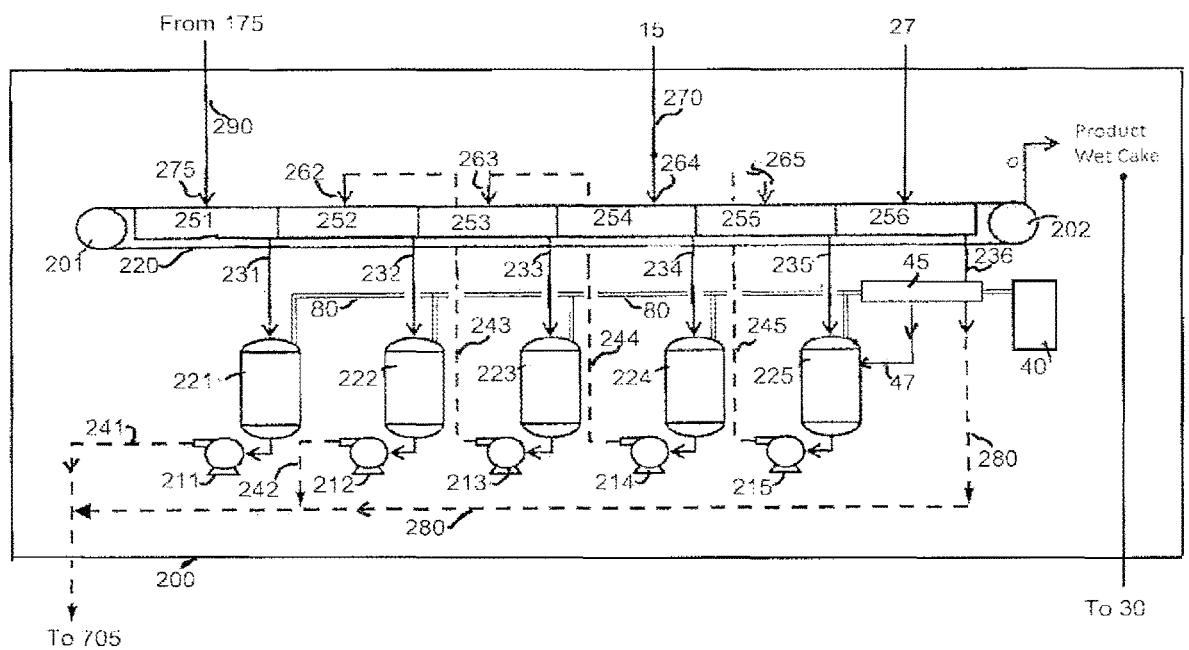
FIG. 2 is a detailed view of a belt filtration system option that can be used as a protein recovery system in accordance with exemplary embodiments of the product recovery system provided herein.

In some embodiments, the product recovery system 1000 includes a product separation system 10 containing a belt filtration system 200. FIG. 2 is a detailed view of an indexing belt filter filtration option that can be included in the product recovery system provided herein. The indexing belt filter 220 receives the processed slurry from the upstream dewatering device 170 via line 175. The processed slurry is discharged onto the indexing belt filter at 251 (stage 1) and creates a thin film of wetcake that advances along the length of the conveyor belt. As the conveyor belt advances, the solid protein wet-cake material is washed at 252, 253 and 254 (stages 2A, 2B and 2C, respectively) using a countercurrent scheme of recycled filtrate washes. As the conveyor advances, the washes are increasingly more pure until the last stage 254 (stage 2C), where the wetcake is washed with fresh organic solvent producing a washed wetcake. The indexing belt filtration system was determined to be highly efficient at removing the oils from the solids. After three equivalent steps, the oil content realized from the washed cake was 6 times greater than that of the reslurried cake from an equivalent batch process.

At least a portion of the washed wetcake can be introduced into the optional product recycle cell 255 (stage 3). The optional product recycle cell 255 of stage 3 can operate to receive a recycle feed stream, thereby enriching the washed wetcake. In some embodiments, the washed wetcake can have an average residence time on the order of at least 2-10 minutes in the product recycle cell of stage 3. The residence time of the washed wetcake in the product recycle cell 255 of stage 3 may vary depending on the equipment used in product separation system 10 of the product recovery system 1000 provided herein. After the time in the product recycle cell 255 is complete, a washed and enriched wetcake can be discharged from the product recycle cell 255 of stage 3. In some embodiments, the washed wetcake bypasses the product recycle cell 255 of stage 3, resulting in a washed (but not enriched) wetcake.

The washed wetcake, or washed and enriched wetcake, then advances to an intermediate drying stage 256 on the belt where a drying gas is applied to the washed wetcake or washed and enriched wetcake in addition to vacuum from beneath the belt filter 220 via common vacuum source 40 to yield a low-moisture product wetcake. The drying gas can be introduced into the product drying cell 256 of stage 4 through inlet 27 and can have an initial temperature (measured at the point of entry as the drying is being introduced into the product drying cell) of at least about 20° C., or a temperature in the range of from about 20° C. to about 80° C.

The drying gas introduced into the product drying cell 256 of stage 4 can be any gas capable of removing at least a portion of the liquid from the washed wetcake or washed and enriched wetcake. The gas can be an inert gas. In some embodiments, the drying gas introduced into the product drying cell 256 of stage 4 can include, for example, argon, nitrogen, carbon dioxide, compressed air or any combination thereof. Drying gas and vapors and condensable liquids removed from the washed wetcake or washed and enriched wetcake can exit the product drying cell 256 of stage 4 via outlet 236, and can exit in a liquid phase, a vapor phase, or a combination of liquid and vapor phases. Outlet 236 is connected to vapor condenser 45. Condensed liquids can be returned to product recycle receiver 225 via line 47 or can be removed from the filtration system via outlet 280.

After sufficient drying (where the percentage of residual solvent in the product cake can be approximately equal to or less than 40%, or less than 30%, or less than 20%), the recovered protein product, a low-moisture wetcake, can exit the product drying cell 256 of stage 4 via outlet O of product separation system 10. In some embodiments, the residence time of the wetcake in the product drying cell 256 is on the order of at least 2-30 minutes. In some embodiments, the wetcake is retained within the product drying cell of stage 4 until the liquid content of the wetcake is less than 30 wt %, or less than 25 wt %, or 20 wt % or less. In some embodiments, the recovered protein product can continue to lose moisture as it travels the length of the conveyor belt filter 220 from the end of vacuum box 256 until it exits the product drying cell via outlet O. The recovered protein product from outlet O can be recovered on discharge stage 30.

The protein product wetcake can be transported from discharge stage 30 transport line 35 to dryer unit 800. The protein product wetcake is dried in dryer unit 800 to a target solvent concentration. In some embodiments, the protein product wetcake it dried to a moisture content of about 10 wt % or less, or about 5 wt % or less, or about 1 wt % or less, less than about 0.5 wt %. In some embodiments, the wetcake is dried until the amount of residual organic solvent is reduced to about 1 wt % or less, or less than 0.5 wt %. The dried protein product is removed from the dryer unit 800 and then subjected to a particle reduction operation using a milling unit 815. In some embodiments, the milling unit 815 includes a micronizing device or jet mill device.

Spent filtrates from the indexing belt filter operation of 200 are continuously transferred to can be recovered by liquid phase processing unit 705, which can include an absorber, followed by treatment in the separation unit 715, which can include a centrifuge and/or distillation unit. In some embodiments, separation unit 715 includes a distillation unit.

In some embodiments, the wetcake within the product separation system 10 is washed with a product wash stream at vacuum box 254 via product wash inlet 15. The product wash stream can be supplied to the product separation system 10 via supply line 189 from virgin solvent tank 180 or via line 750 from recovered solvent tank 740. An in-line mixer can blend the wash streams from lines 189 and 750 prior to entering product wash inlet 15. The product wash stream introduced into product separation system 10 can wash at least a portion of the wetcake. In some embodiments, the product wash stream can have an initial temperature upon being introduced into product separation system 10 of at least about 25° C., or a temperature in the range of from about 25° C. to about 75° C. or a temperature of 72° C. or less. In some embodiments, the washing steps are performed using a washing liquid that can be in the temperature range from about 40° C. to about 80° C., or from about 50° C. to about 72° C., or from about 65° C. to about 72° C., or at a temperature of about 72° C., 71° C., 70° C., 69° C., 68° C., 67° C., or 65° C.

The residence time of the wetcake in the product wash cell 254 of stage 2 may vary depending on the equipment used in product separation system 10. In some embodiments of the methods and systems provided herein, the initial wetcake can have an average residence time between 2-5 minutes in wash stage 2, or can have a shorter residence time, such as an average residence time in the range of about 5 seconds to about 2 minutes in wash stage 2.

In some embodiments, the product wash stream can include a solvent, such as an aliphatic hydrocarbon, e.g., hexane, an alcohol, an ester, water or any combination thereof. In some embodiments, the solvent includes a combination of water with an organic solvent, such as an aliphatic hydrocarbon, an alcohol, an ester, or a combination thereof. Any ratio of water to organic solvent can be used in the product wash stream, e.g., from 99:1 water:organic solvent to 1:99 water:organic solvent, including up to 100 percent solvent or 100 percent water.

Any amount of product wash stream can be used to wash the retained wetcake resulting from processed slurry. In some embodiments, the weight ratio of the product wash stream introduced into product separation system 10 to the solids from the solid phase separated from the processed slurry can be at least about 0.2:1, or in the range of from about 0.2:1 to about 5:1, where these ratios are expressed in unit volume of solvent to weight of solid starting material.

In some embodiments of the present invention, the product separation system 10 of the product recovery system 1000 can include an optional product recycle section to enrich the retained wetcake from the solid phase separated from the processed slurry. In the recycle section, wash filtrates can be recycled back into the product separation system 10 in order to capture any protein particles that may have passed through into the filtrate. For example, during initial formation of the wetcake within the product separation system 10 containing a filter on the surface of which the wetcake is building, some protein particles may have passed through or by-passed the filter. By recycling the filtrates in this manner, any initially lost protein particles can be recaptured, thereby enriching the wetcake with additional protein particles. After enriching at least a portion of the wetcake of solid particles, an optional depleted recycle liquid can be withdrawn from product separation system 10. The recycle feed stream can have an initial temperature in the range of from about 20° C. to about 80° C.

The vacuum belt filter system 200 depicted in FIG. 2 includes a conveyor belt filter 220, a common vacuum source 40 connected to a plurality of vacuum boxes. The number and size of the vacuum boxes (stations) can be modulated and customized to suit the different types of raw material that can be used. In the embodiment depicted, the conveyor belt filter 220 includes six vacuum boxes: a separation cell stage 1 vacuum box 251, product wash cell stage 2A vacuum box 252, a product wash cell stage 2B vacuum box 253, a product wash cell stage 2C vacuum box 254, an optional product recycle cell stage 3 vacuum box 255, and a product drying cell stage 4 vacuum box 256. As illustrated in FIG. 2, the separation cell of stage 1 can be defined by the horizontal length of the separation cell stage 1 vacuum box 251. The product wash cell of stage 2 can be defined by the combined horizontal lengths of vacuum boxes 252, 253 and 254 of product wash cell stages 2A, 2B, and 2C. The optional product recycle cell of stage 3 can be defined by the horizontal length of the product recycle cell stage 3 vacuum box 255. The product drying cell of stage 4 can be defined as the horizontal length beginning at the start of the product drying cell stage 4 recycle vacuum box 256 and ending at the end of conveyor belt roller 202. A discharge stage 30 can be provided following the product drying cell of stage 4.

Referring still to FIG. 2, conveyor belt filter 220 can include a filter media such as, for example, a filter cloth. The filter cloth can be made from any compatible material, such as a metal mesh screen, nylon, polyester, polysulfone, polytetrafluoroethylene polypropylene, and polyamide. In some embodiments, the filter cloth has an internal pore size of 100 μm or less, such as from about 35 μm to about 100 μm, or from about 10 μm to about 50 μm. On this filter the processed slurry can be separated by drawing the liquid phase of the slurry through the filter cloth by means of vacuum, forming a protein wetcake on the surface of the filter. The protein wetcake is transported with the moving vacuum belt filter cloth. The speed of transport can be varied to increase or decrease the amount of time the protein wetcake reside in each of the product wash cells, optional product recycle cell, and product drying cell. The protein wetcake can be washed with product wash stream in the product wash cells of stage 2, and the wash filtrates are continually drawn through the filter cloth as a result of the vacuum in the vacuum boxes.

Fluid flow through the filter media can be caused by creating a pressure differential across the filter media. In some embodiments, the pressure differential across the filter media can be created at least in part by common vacuum source 40. Fluid flow through the filter cloth can be discharged into the vacuum boxes of stages 1-4 (vacuum boxes 251 through 256).

The vacuum belt filter system 200 depicted in FIG. 2 can include a processed slurry supply line 290 in fluid communication with dewatering device 170 via line 175 for depositing processed slurry onto conveyor belt filter 220 via applicator 275. The embodiment depicted in FIG. 2 includes a product wash feed line 270 in fluid communication with wash stage 2C of the product wash cell 254 of stage 2, and a drying gas in fluid communication with the product drying cell 256 of stage 4. As depicted, the product wash cell of stage 2 is divided into an initial wash stage 2A, an intermediate wash stage 2B, and a final wash stage 2C. Initial wash stage 2A can be defined by the horizontal length of the product wash cell stage 2A vacuum box 252, intermediate wash stage 2B can be defined by the horizontal length of the product wash cell stage 2B vacuum box 253, and final wash stage 2C can be defined by the horizontal length of the product wash cell stage 2C vacuum box 254.

In operation, the processed slurry can enter the separation cell of stage 1, such as via applicator 275. The processed slurry introduced into the separation cell of stage 1 can be separated into a solid phase, which forms an initial wetcake on the filter media on conveyor belt filter 220, and a liquid phase, which can be discharged out of the separation cell into stage 1 vacuum box 251. The liquid phase collected in stage 1 vacuum box 251 can be routed to receiver 221 via discharge line 231. Receiver 221 is in fluid communication with common vacuum source 40 via an overhead common vacuum line 80 to create reduced pressure conditions in receiver 221, which in turn can at least partially create the above-mentioned pressure differential across conveyor belt filter 220 in vacuum box 251. Receiver 221 can contain therein a vapor phase and the separated liquid phase from the processed slurry.

At least a portion of the vapor phase in receiver 221 can be removed via common vacuum line 80 and can be routed to common vacuum source 40. In some embodiments, a vapor condenser 45 can be disposed between common vacuum line 80 and common vacuum source 40. The vapor condenser 45 can operate to remove any liquid in line so as to prevent liquid from entering common vacuum source 40. Vacuum box 256 can be configured so that any liquid collected in vacuum box 256 of stage 4 can be directed to vapor condenser 45 via outlet 236. The condensed liquid produced in vapor condenser 45 can be routed to liquid phase processing unit 705. The liquid phase in receiver 221 can be discharged via line 241 and can be routed to liquid phase processing unit 705. The liquid phase can be withdrawn from the liquid phase receiver 221 via pump 211 and can be discharged via line 241 to liquid phase processing unit 705.

Still referring to FIG. 2, upon obtaining a desired height of initial wetcake in the separation cell of stage 1, vacuum box 251 is disengaged and belt rollers 201 and 202 are engaged to advance conveyor belt filter 220 so that initial wetcake can enter the product wash cell of stage 2. In the embodiment of FIG. 2, initial wetcake can have a thickness in the range of from about 0.25 to about 5 inches, or in the range of from about 0.5 to about 4 inches, or in the range of from 1 to 3 inches.

In the product wash cell of stage 2, initial wetcake can be washed with a product wash stream. In the embodiment shown in FIG. 2, a counter-current wash is illustrated. Product wash stream enters final wash stage 2C via product wash feed line 270 and is applied to the wetcake via applicator 264 to thereby form a washed wetcake. The product wash stream entering wash stage 2C can be fresh solvent, which can be transported from solvent supply tank 180 via supply line 189, or can be recovered solvent delivered by supply line 750, or a combination thereof. The product wash stream can include a solvent, such as an aliphatic hydrocarbon, e.g., hexane, an alcohol, an ester, water or any combination thereof. In some embodiments, the solvent includes a combination of water with an organic solvent, such as an aliphatic hydrocarbon, an alcohol, an ester, or a combination thereof. Any ratio of water to organic solvent can be used in the product wash stream, e.g., from 99:1 water:organic solvent to 1:99 water:organic solvent, including up to 100% solvent or 100% water.

Application of the product wash stream via applicator 264 to the wetcake in the product wash cell at stage 2C and downward through the filter media of conveyor belt filter 220 results in a first wash liquid, which can be discharged into vacuum box 254 of stage 2C of the product wash cell. The first wash liquid collected in vacuum box 254 can be routed to first wash liquid receiver 224 via discharge line 234. First wash liquid receiver 224 can communicate with common vacuum source 40 to create reduced pressure conditions in the first wash liquid receiver 224, which in turn can at least partially create a pressure differential across conveyor belt filter 220 at vacuum box 224, which is connected to first wash liquid receiver 224 via discharge line 234. First wash liquid receiver 224 can contain therein a vapor phase and the first wash liquid. At least a portion of the vapor phase in the first wash liquid receiver 224 can be removed via common vacuum source line 80. At least a portion of the first wash liquid can be withdrawn from first wash liquid receiver tank 224 via vacuum pump 214 and can be applied to the wetcake in stage 2B via wash line 244 and applicator 263. The first wash liquid also can be discharged to liquid phase processing unit 705 via appropriating pipes or tubing (not shown).

In some embodiments, at least a portion of the first wash liquid can be transferred via pump 214 and wash line 244 to intermediate wash stage 2B to thereby wash at least a portion of initial wetcake by application to initial wetcake via applicator 263, forming a second wash liquid, which can be discharged downward through the filter media of conveyor belt filter 220 at stage 2B into vacuum box 253. The second wash liquid collected in vacuum box 253 can be routed to second wash liquid receiver 223 via discharge line 233. Second wash liquid receiver 223 can communicate with common vacuum source 40 to create reduced pressure conditions in second wash liquid receiver 223, which in turn can at least partially create a pressure differential across conveyor belt filter 220 at stage 2B via vacuum box 253. Second wash liquid receiver 223 can contain therein a vapor phase and the second wash liquid. At least a portion of the vapor phase in second wash liquid receiver 223 can be removed via common vacuum line 80 and can be routed to common vacuum source 40. At least a portion of the second wash liquid can be withdrawn from the second wash liquid receiver 223 via vacuum pump 213 and can be applied to the wetcake in stage 2A via line 243 and applicator 262. The second wash liquid also can be discharged to liquid phase processing unit 705 via appropriating pipes or tubing (not shown).

In some embodiments, at least a portion of the second wash liquid can be transferred to initial wash stage 2A to thereby wash at least a portion of initial wetcake at stage 2A, forming a final wash liquid, which can be discharged downward through the filter media of conveyor belt filter 220 into vacuum box 252 of stage 2A. The final wash liquid collected in vacuum box 252 of stage 2A can be routed to final wash liquid receiver 222. Final wash liquid receiver 222 can communicate with common vacuum source 40 to create reduced pressure conditions in final wash liquid receiver 222, which in turn can at least partially create a pressure differential across conveyor belt filter 220 at vacuum box 252. Final wash liquid receiver 222 can contain therein a vapor phase and the final wash liquid. At least a portion of the vapor phase in final wash liquid receiver 222 can be removed by common vacuum source 40 via common vacuum line 80. The final wash liquid in final wash liquid receiver 222 can be discharged via pump 212 via lines 242, 280 and 241 to liquid phase processing unit 705.

In the embodiment illustrated in FIG. 2, the initial wetcake can have an average residence time of less than about 6 minutes, or less than about 2 minutes, less than about 1.5 minutes, or less than 1 minute in the product wash cell of stage 2. In some embodiments, the initial wetcake is washed in each of stages 2A, 2B and 2B for about 2 minutes or less for each station. In some embodiments, the residence time of initial wetcake in stage 2C is equal to the sum of the residence time of the initial wetcake in stages 2A and 2B. After suitable washing (e.g., 1-3 displacement washes), in the product wash cell of stage 2, the conveyor belt rollers 201 and 202 are engaged to advance conveyor belt filter 220 so that washed wetcake can enter optional recycle stage 3. In some embodiments, the conveyor belt rollers 201 and 202 are engaged to advance conveyor belt filter 220 so that washed wetcake enters the product drying cell of stage 4.

In embodiments where the conveyor belt filter 220 is advanced to optional recycle stage 3, washed wetcake can be enriched by application of a recycle feed from product recycle receiver 225 via line 245 and applicator 265 by pump 215 to thereby form a washed and enriched wetcake. The recycle feed can include the filtrates recovered from the product wash cells of stage 2 and/or the recycle feed stream. After application of the recycle feed stream to the washed wetcake it discharges downward through the filter media of conveyor belt filter 220 resulting in a depleted recycle liquid that is collected into vacuum box 255 of recycle stage 3. The depleted recycle liquid collected in vacuum box 255 can be routed back to product recycle receiver via discharge line 235. Product recycle receiver 225 can communicate with common vacuum source 40, such as via common vacuum line 80, to create reduced pressure conditions in product recycle receiver 225, which in turn can at least partially create a pressure differential across conveyor belt filter 220 at vacuum box 255. Product recycle receiver 225 can contain therein a vapor phase and the depleted recycle liquid. At least a portion of the vapor phase in product recycle receiver 225 can be removed via common vacuum line 80 and can be routed to common vacuum source 40.

In some embodiments, the washed wetcake from the slurry can have an average residence time in the product recycle cell of stage 3 on the order of 1-5 minutes, where suitable enriching is performed by recycling solid material that passed through the bed and into the filtrate receiver. In optional recycle stage 3, conveyor belt rollers 201 and 202 can be engaged to advance conveyor belt filter 220 so that washed and enriched wetcake can enter drying stage 4.

In drying stage 4, liquid can be removed from washed wetcake and washed and enriched wetcake by passing a drying gas, from a drying gas supply via drying gas inlet 27, over, across and/or through the washed wetcake or washed and enriched wetcake, thereby producing a final low-moisture protein product wetcake. The drying gas can include, for example, argon, nitrogen, carbon dioxide, compressed air or any combination of these gases. Liquid and/or humid vapor can be removed from stage 4 and from product separation system 10 in general via, e.g., common vacuum line 80, where a vapor condenser 45 is disposed between the common vacuum line 80 and common vacuum source 40. The vapor condenser 45 can operate to remove any liquid in line so as to prevent liquid from entering common vacuum source 40. Condensed liquids produced by vapor condenser 45 can be discharged to liquid phase processing unit 705.

In some embodiments, the average residence time within the product drying cell of stage 4 for the washed wetcake or the washed and enriched wetcake can be less than about 5 minutes. After suitable drying (e.g., when the wetcake has a targeted moisture content, such as a moisture content of from about 20 wt % to about 40 wt %) in drying stage 4 the conveyor belt rollers 201 and 202 can be engaged to advance conveyor belt filter 220 so that final wetcake can discharge from stage 4.

At the end of the product drying cell of stage 4, at least a portion of final low-moisture wetcake recovered protein product can be disengaged from conveyor belt filter 220 and can exit product processing system 10 via outlet O. In some embodiments, a discharge stage 30 can capture and hold the recovered protein product.

In some embodiments, a conveyor belt washing step can be performed after the final low-moisture wetcake recovered protein product is disengaged from conveyor belt filter 220 to wash out any wetcake material that may have adhered to the conveyor belt filter 220. Product wash stream or other wash stream containing similar components, such as, e.g., water, an alcohol, such as ethanol or isopropyl alcohol, an aliphatic hydrocarbon, an alcohol, or an ester or any combination thereof, can be applied to the conveyor belt filter 220 via an applicator to wash the conveyor belt filter 220. In some embodiments, no aliphatic hydrocarbon is used in the device and/or during the processing. In some embodiments, the processes and methods provided herein do not include application of or addition of hexane at any step. Material washed off of conveyor belt filter 220 and the washing liquid used in washing step can be directed to product recycle receiver 225.

Rotary Pressure/Vacuum Drum Filtration

Figure 3:
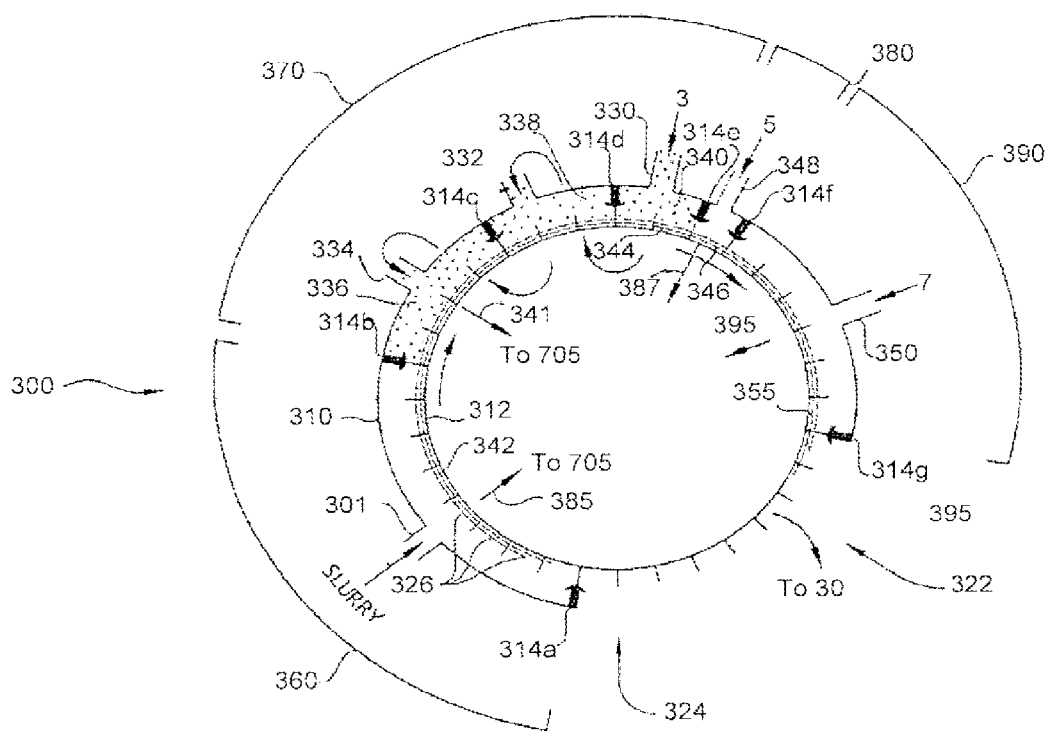
FIG. 3 a detailed view of a rotary drum filtration system option that can be used in accordance with exemplary embodiments of the product recovery system provided herein.

In some embodiments, the product separation system 10 of the product recovery system 1000 provided herein can include a rotary pressure/vacuum drum filtration system 300. Rotary drum filters are known in the art (e.g., see U.S. Pat. Nos. 5,175,355; 5,643,468; 7,470,370; 7,462,736; 7,888,530; 7,897,810; 8,697,906); and 8,859,825). An exemplary rotary pressure/vacuum drum filter is illustrated in FIG. 3. The rotary pressure/vacuum drum filter illustrated in FIG. 3 includes a housing 310 and a rotary drum filter 312 rotatably disposed within housing 310. An annulus is defined between the inside of housing 310 and the outside of rotary drum filter 312. This annulus is divided into various discreet stages by seals 314a through 314g. The separation stage 360 is defined in the annulus between seals 314a and 314b. Wash stage 370 is defined in the annulus between seals 314b and 314e. An optional recycle stage 380 is defined in the annulus between seals 314e and 314f. Drying stage 390 is defined in the annulus between seals 314f and 314g. Housing 310 can be open between seals 314g and 314a. This open portion of housing 310 can include a discharge stage 322 and a filter wash stage 324.

Referring still to FIG. 3, rotary drum filter 312 can define a plurality of filter cells 326 located on the periphery of the drum filter 312. The bottom of each filter cell 326 can be formed of a filter media (e.g., a synthetic cloth, single-layer metal, or multi-layer metal). Fluid flow through the filter media can be caused by creating a pressure differential across the filter media. Each filter cell 326 has its own outlet for discharging fluids inwardly towards the axis of rotation of rotary drum filter 312. The outlets of axially-aligned filter cells 326 can be manifolded. The manifolds (not shown) can rotate with the rotary drum filter 312 and can communicate with a service/control head (not shown) which can collect the fluids from the manifolds in a manner that allows the fluids discharged from stages 360, 370, 380, and 390 to be kept separate. The discharged fluids also can be combined and discharged to liquid phase processing unit 705.

Housing 310 can include a slurry inlet 301 that can be in fluid communication with separation stage 360, a wash feed inlet 330 that can communicate with wash stage 370, an optional recycle feed inlet 348 that can be in fluid communication with optional recycle stage 380, and a drying gas inlet 350 that can be in fluid communication with drying stage 390. Wash stage 370 can be divided into an initial wash stage 336, an intermediate wash stage 338, and a final wash stage 340, where intermediate wash stage 338 is separated from initial wash stage 336 by seal 314c and final wash stage 340 is separated from intermediate wash stage 338 by seal 314d. Housing 310 and rotary drum filter 312 can be configured to permit filtrate discharged from final wash stage 340 to enter intermediate wash stage 338, and filtrate discharged from intermediate wash stage 338 to enter initial wash stage 336 to product a counter-current wash.

In operation, the processed slurry can enter separation stage 360 via slurry inlet 301. The processed slurry introduced into separation stage 360 can form an initial wetcake 342 in filter cells 326 on the periphery of rotary filter drum 312. In separation stage 360, the liquid phase separated from the processed slurry can be discharged radially inward from the bottom of each filter cell 326. The liquid phase collected from separation stage 360 can be discharged from the apparatus via discharge line 385. Upon obtaining a desired height of initial wetcake 342 in separation stage 360, rotary drum filter 312 can rotate so that initial wetcake 342 enters wash stage 370. In the embodiment illustrated in FIG. 3, initial wetcake 342 can have a thickness in the range of from about 0.1 to about 10 inches, or in the range from about 2 to about 8 inches, or in the range of from about 3 to about 7 inches, or in the range of from 4 to 6 inches.

In wash stage 370, initial wetcake 342 can be washed with a product wash stream 3 entering final wash stage 340 via wash feed inlet 330 and applied to initial wetcake 342 to thereby form a washed wetcake 344. The first wash filtrate from final wash stage 340 can then be transferred to intermediate wash stage 338 via first wash filtrate inlet 332 and applied to the wetcake to form a second wash liquid, and the second wash liquid from intermediate wash stage 338 can then be transferred to initial wash stage 336 via second wash filtrate inlet 334 and applied to the wetcake. The final wash liquid from initial wash stage 336 can then be discharged from product processing system 10. For example, as shown in FIG. 3, the final wash liquid can be discharged via discharge line 341 to liquid phase processing unit 705.

In the embodiment illustrated in FIG. 3, the wetcake containing the separated solid phase of the processed slurry containing protein particles can have an average residence time of less than about 2 minutes, or less than about 1 minute, or less than about 40 seconds, or less than 25 seconds in wash stage 370. After suitable washing (which can be defined by using 1-3 displacement washes) in wash stage 370, rotary drum filter 312 can rotate so that washed wetcake 344 can enter optional recycle stage 380.

Still referring to FIG. 3, in optional recycle stage 380, washed wetcake 344 can be optionally enriched with a recycle feed stream 5 entering optional recycle stage 380 via recycle feed inlet 348 to thereby form a washed and enriched wetcake 346. After recycle, depleted recycle liquid can be discharged from product processing system 10. For example, as illustrated in FIG. 3, depleted recycle liquid can be discharged via discharge line 387. In the embodiment illustrated in FIG. 3, the wetcake can have an average residence time of less than about 2 minutes, or less than about 1 minute, or less than about 40 seconds, or less than 25 seconds in optional recycle stage 3. After suitable enriching, where suitable enriching is performed by recycling solid material that passed through the rotary drum filter into the filtrate receiver in optional recycle stage 3, rotary drum filter 312 can rotate so that washed and enriched wetcake 346 can enter drying stage 390.

In drying stage 390, liquid can be removed from washed wetcake 344 or washed and enriched wetcake 346 by passing a drying gas 7, entering via gas inlet 350, around and/or through washed wetcake 344 or washed and enriched wetcake 346, thereby producing a final low-moisture wetcake protein product 355. The drying gas 7 introduced into inlet 350 can include, for example, argon, nitrogen, carbon dioxide, compressed air or any combination thereof.

In the embodiment illustrated in FIG. 3, the washed wetcake 344 or washed and enriched wetcake 346 can have an average residence time of less than about 2 minutes, or less than about 1 minute, or less than about 45 seconds in drying stage 390. After suitable drying (e.g., to a targeted moisture content, such as a wetcake moisture content of approximately 20-40 wt %) in drying stage 390, rotary drum filter 312 can rotate so that final low-moisture wetcake protein product 355 can be discharged to discharge stage 322 via line 390.

In discharge stage 322, at least a portion of the final low-moisture wetcake protein product 355 can be disengaged from rotary drum filter 312 and can exit product separation system 10 via discharge line 395. Rotary drum filter 312 can then rotate into filter wash stage 324, where any solid particles remaining in filter cells 326 can be removed. In some embodiments, the material washed out of filter cells 326 in filter wash stage 324 and the wash liquid can be added to recycle stream 5.

Spent filtrates from rotary drum filter extraction unit 300 are continuously removed from the extraction unit 300 to liquid phase processing unit 705, which can include an absorber, followed by treatment in the separation unit 715, which can include a distillation unit.

It will be understood by one skilled in the art that many different configurations of rotary pressure drum filters are possible, any of which can be used in the present invention. Examples of suitable, commercially available rotary pressure drum filters that can be used in product separation system 10 include, but are not limited to, a BHS-FEST Rotary Pressure Filter, available from BHS-Sonthofen GmbH, D-87527, Sonthofen, Germany; and Rotapress FRP continuous rotary filters, available from 3VTech, Bergamo, Italy.

Immersion Extraction Filtration

In some embodiments, the product separation system 10 of the product recovery system 1000 can include an immersion extraction filtration system 400. An exemplary immersion extraction filtration system is described in U.S. Pat. No. 4,751,060. The extractor includes a plurality of pools through which a solid to be extracted is moved in a counterflow direction, usually by a plurality of conveyor belts. The belts move the material across the bottom of the extractor, maintaining the solid material immersed in solvent, which is flowing in a counter-current direction. Commercial immersion extraction filtration devices are available, e.g., the Model IV Extractor from Crown Iron Works (Minneapolis, MN).

Figure 4:
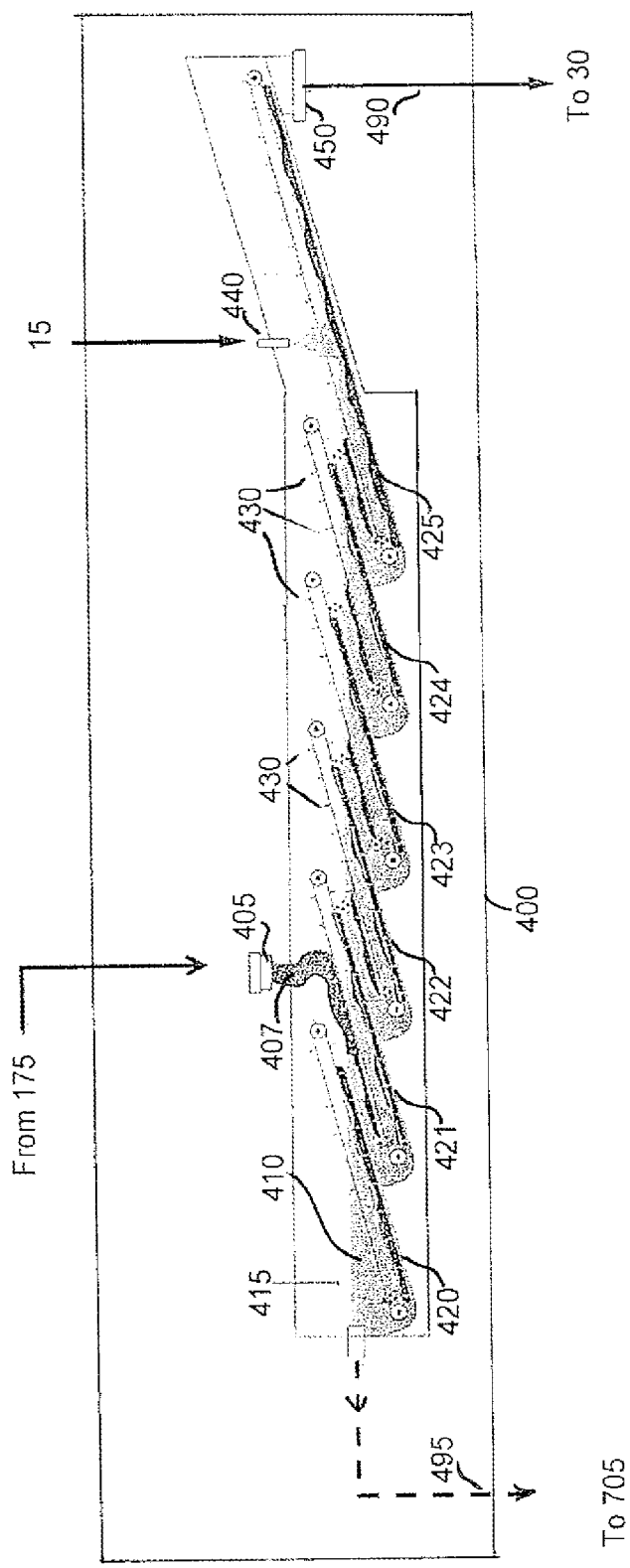
FIG. 4 is a detailed view of an immersion extraction system option that can be used in accordance with exemplary embodiments of the product recovery system provided herein.

FIG. 4 is a detailed view of an exemplary immersion extraction filtration option that can be included in the product recovery system provided herein. In the system illustrated, 6 separate conveyor belts 420, 421, 422, 423, 424, and 425 moving in the same direction (counter-clockwise is illustrated to maintain the material moving through solvent bath 410 and under the upper level 415 of the solvent bath 410) pull the deposited material through the solvent bath 410. Each conveyor belt has a first end and a second end. Except for the last conveyor belt in the system, the second end of each conveyor belt extends over at least a portion of the first end of the next conveyor belt. Each conveyor belt includes protrusions 430 that extend above the conveyor belt and are brought into contact with a bottom surface of the filtration unit as the conveyor belts moves and can push slurry material through the unit while the material remains submerged and in intimate contact with the solvent.

The immersion extraction unit 400 receives the processed slurry from the upstream dewatering device 170 via line 175. The processed slurry is discharged to the immersion extraction unit 400 via entry port 405. The processed slurry maintains intimate contact with wash solvent while advancing towards the discharge 450 of the immersion extraction unit due to the movement of each of the conveyor belts. Filtrate is removed from the lower compartment of the immersion extraction unit via filtrate outlet line 495 and is then discharged to the liquid phase processing unit 705.

Once deposited on the last conveyor belt, the processed slurry forms a protein product wetcake as the liquid phase of the slurry is removed. The protein product wet cake is washed with product wash stream from product wash inlet 15 and applied to the protein product wetcake via applicator 440 and the washed protein product wetcake is then discharged from the immersion extraction unit via port 450 and transferred to discharge stage 30 via line 490. The protein product wetcake is transferred to dryer unit 800 and dried to a moisture content of about 10 wt % or less, or about 5 wt % or less, or about 1 wt % or less, or less than about 0.5 wt %. In some embodiments, the wetcake is dried until the amount of residual organic solvent is reduced to about 1 wt % or less, or less than 0.5 wt %. The dried protein product is removed from the dryer unit 800 and then subjected to a particle reduction operation using mill unit 815, which can include a micronizing device or jet mill device. Spent filtrates from the immersion extraction unit 400 can be recovered by directing the material to liquid phase processing unit 705, which can include an absorber, followed by treatment in the separation unit 715, which can include a centrifugation unit and/or a distillation unit.

Percolation Extractor

In some embodiments, the product separation system 10 of the product recovery system 1000 can include a percolation extractor system 500. Percolation extractors are known in the art (e.g., see U.S. Pat. Nos. 4,144,229; and 4,859,371). Typical percolation extractors include a conveyor belts that slowly moves a material to be extracted over a stationary screen. As the conveyor moves, a washing solvent is applied to the upper surface of the material on the conveyor, and the washing solvent percolates down through the material and through the screen. Commercial percolation extractor devices are available, e.g., the Model III Percolation Extractor and the Model V Percolation Extractor from Crown Iron Works (Minneapolis, MN).

Figure 5:
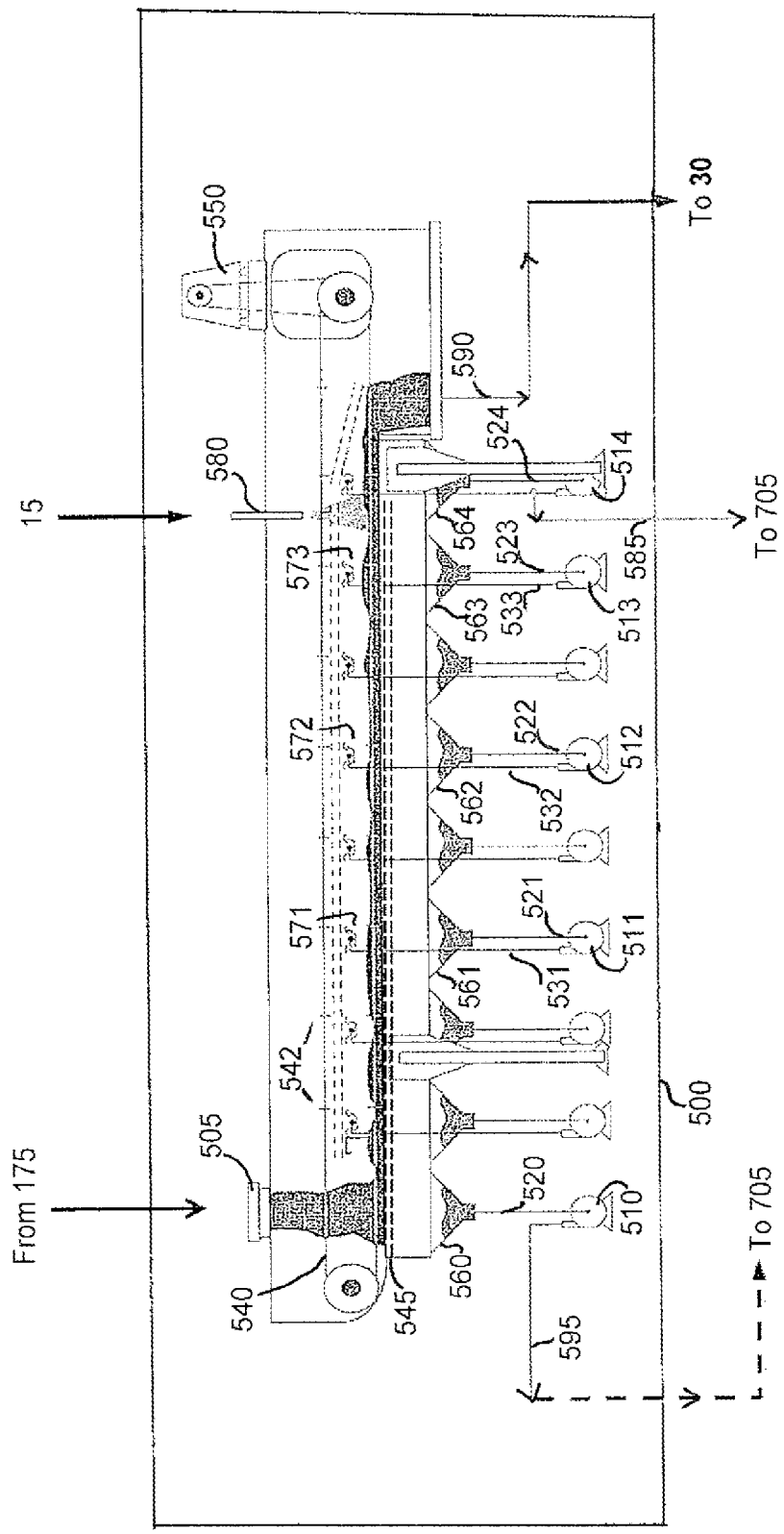
FIG. 5 a detailed view of a percolation extraction system option that can be used in accordance with exemplary embodiments of the product recovery system provided herein.

FIG. 5 is a detailed view of an exemplary percolation extraction filtration option that can be included in the product recovery system provided herein. The percolation extraction unit 500 receives the processed slurry from the upstream dewatering device 170 via line 175. The processed slurry is discharged to the percolation extraction unit 500 via entry port 505 where the slurry is deposited on a stationary screen 545 and advances towards the discharge of the percolation extraction unit 500 by the belt protrusions 542 on conveyor belt 540. Pump 510 creates a pressure differential between the applied processed slurry and the collection compartment 560 forming a protein product wetcake, the filtrate being removed into collection compartment 560 and removed from system 500 via pump 510 and line 595 to liquid phase processing unit 705. The protein product wetcake advances by movement of belt 540 across stationary screen 545 and is washed until it exits percolation extraction unit 500. The conveyor belt 540 is advanced by motor assembly 550.

Filtrate is drawn out of the protein product wetcake as it moves across the screen by pumps (e.g., pumps 511, 512 and 513 in FIG. 5) and collected in filtrate receiving compartments (e.g., compartments 561, 562 and 563 in FIG. 5). The collected filtrate is recycled back into the percolation unit 500 and used to wash the protein product wetcake (e.g., via applicators 571, 572 and 573 in FIG. 5). At the last stage prior to exiting system 500, protein product wetcake is washed with product wash from product wash inlet 15 via applicator 580. Filtrate from this wash is collected into receiving compartment 564 via the pressure differential created by pump 514 and the filtrate is removed from filtrate receiving compartment 564 by pump 514 and discharged to liquid phase processing unit 705.

In some embodiments (not shown in FIG. 5), the device can be configured with appropriate lines or tubing so that the protein product wetcake be washed in a counter-current method. For example, referencing the item numbers shown in FIG. 5, in one embodiment, the filtrate collected in filtrate receiving compartment 563 can be directed to filtrate receiving compartment 562, which then is applied to wetcake via applicator 572. The filtrate collected in filtrate receiving compartment 562 then can be directed to filtrate receiving compartment 561, which then is applied to wetcake via applicator 571.

In another example (not shown in FIG. 5), the device can be configured with appropriate lines or tubing so that the protein product wetcake can be washed with a recovered filtrate produced by the washing of the wetcake with product wash applied using applicator 580. For example, referencing the item numbers shown in FIG. 5, recovered filtrate produced by the washing of the wetcake with product wash applied using applicator 580 can be collected into filtrate receiving compartment 564 using pump 514. The filtrate then can be pumped via pump 514 to applicator 573, which applies the filtrate to the upper surface of the wetcake. Filtrate produced by the washing of the wetcake with filtrate applied by applicator 573 can be collected into and removed from filtrate receiving compartment 563 by pump 513. The filtrate then can be pumped via line 533 to applicator 572, which applies the filtrate to the upper surface of the wetcake. Filtrate produced by the washing of the wetcake with filtrate applied by applicator 572 can be collected into and removed from filtrate receiving compartment 562 by pump 512. The filtrate then can be pumped via line 532 to applicator 571, which applies the filtrate to the upper surface of the wetcake.

Constant washing of the wetcake allows a high degree of mass transfer to effect purification of the wetcake as it moves through the unit. The wetcake advances toward the end of the percolation extraction unit where it is ultimately given a fresh solvent wash with product wash via wash applicator 580. Filtrate is collected in filtrate receiving compartment 564 and protein product wetcake is then discharged from percolation extraction unit 500 via exit 590 onto discharge stage 30. The protein product wet cake then can be transferred to a drying unit 800 via transport line 35. The protein product wetcake is dried to a targeted solvent concentration. In some embodiments, the protein product wetcake is dried to a moisture content of about 10 wt % or less, or about 5 wt % or less, or about 1 wt % or less, or about 0.5 wt % or less. In some embodiments, the wetcake is dried until the amount of residual organic solvent is reduced to about 1 wt % or less, or less than 0.5 wt %. The dried protein product wetcake is removed from the dryer unit 800 and then subjected to a particle reduction operation using a mill unit 815, which can include micronizing device or jet mill device. Spent filtrates from percolation extraction unit 500 are continuously removed from the extraction unit 500 by pump 510 via line 595 to liquid phase processing unit 705, which can include an absorber, followed by treatment in the separation unit 715, which can include a centrifugation unit and/or a distillation unit.

Screw Press System

Figure 6A:
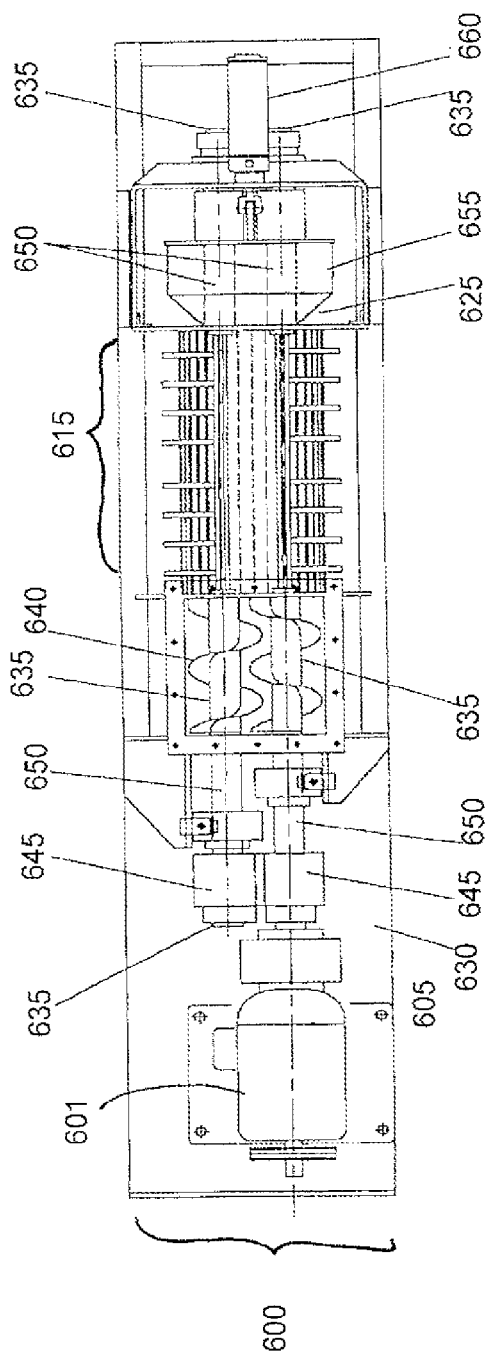
FIG. 6A is a schematic top view and FIG. 6B is a schematic side view of a screw press system option that can be used in accordance with exemplary embodiments of the product recovery system provided herein.
Figure 6B:
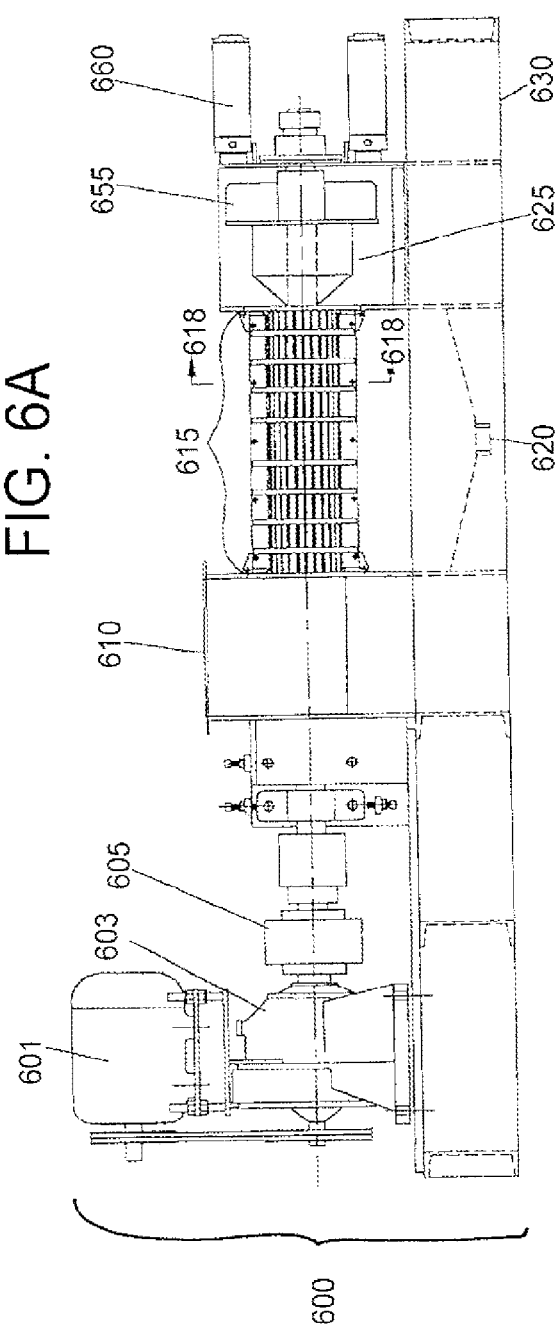

In some embodiments, the product separation system 10 of the product recovery system 100 provided herein can include a screw press system. An exemplary screw press system 600 is illustrated in FIGS. 6A and 6B. FIG. 6A shows a schematic top view of a twin screw press 600. The screw press illustrated in FIG. 6A includes a motor 601 attached to frame 630. The motor 601 connects to a gear reduction drive 603 (not shown in FIG. 6A) which is connected to a shaft coupling 605 which is connected to at least one of screw shaft 650. Gear boxes 645 can connect screw shafts 650 of dual overlapping screws 635 (a single screw is optional but not shown) with continuous feeder flighting 640 and drive the screw action, directing processed slurry into screen chamber 615. Through one or more shaft couplings 605 the gearboxes drive the screws 635. Any necessary adjustments of the system can be accomplished by adjuster 660, which can include springs, bladders, counterweights, and hydraulic cylinders to provide adjustment, e.g., of back pressure, during press operation. Expelled liquid drains through screen chamber 615 and can be removed via liquid drain 620. Wetcake discharges at press cake discharge 625 before restraining cone 655.

FIG. 6B shows a schematic side view of a twin screw press 600. The screw press 600 illustrated in FIG. 6B includes a motor 601, a gear reduction drive 603, a shaft coupling 605 connecting dual overlapping screws (however, a single screw is optional), an inlet port 610 for introducing the processed slurry, a screen chamber 615, a solids restrainer 618, a liquid drain 620, a press cake discharge 625, an adjuster 660 and a frame 630. Press liquid drains from liquid drain 620 while press cake can be collected from press cake discharge 625. The screw press 600 can further include a liquid or filtrate discharge line attached to liquid drain 620 to direct the filtrate to liquid phase processing unit 705, and a solids discharge line for discharging the pressed wet cake from press cake discharge 625 to discharge stage 30. The figures show a screw press in a horizontal configuration. Vertical configurations, with material flowing either upward or downward, also can be used.

The processed slurry containing the raw fish and organic solvent, are dispensed into the screw press liquid inlet port 610. The screws 635 rotate in a manner to compress the combined liquid and solids comprising the slurry. Liquid filtrate is discharged from screw press 600 via liquid drain 620 and transferred to the solvent recovery system (SLR) for subsequent recovery of the organic solvent and omega-3 oil.

Solid wetcake product is discharged from the screw press 600 via press cake discharge 625 with a moisture content in the range of 20-40 wt %. In some embodiments, the solid wetcake can be returned to slurry tank 150 containing fresh or recovered organic solvent via appropriate lines, tubing or piping (not shown). The combined mixture can be stirred in slurry tank 150 until a homogeneous slurry is achieved, and the homogeneous slurry can then transferred to the dewatering device 170 where separation of the liquid filtrate and solid wet cake occur. The combination of preparing the slurry in conjunction with transferring the slurry to the dewatering device 170 can be optionally performed several times until the desired level of water removal is achieved. In similar embodiments, water removal levels of 75% have been achieved. The final protein product wet cake is then transferred to product separation system 10 for further processing, and exits product separation system 10 via outlet O and ultimately is transported to a drying unit 800 where the solid product is dried to a moisture content of 10 wt % or less, or 5 wt % or less, of 1 wt % or less, or less than 0.5 wt %. In some embodiments, the wetcake is dried until the amount of residual organic solvent is reduced to about 1 wt % or less, or less than 0.5 wt %.

Decanter Centrifuge System

In some embodiments, the product separation system 10 of the product recovery system 100 provided herein can include a decanter centrifuge system 675. Any of the various configurations of decanter centrifuges can be included in decanter centrifuge system 675 (see, e.g., U.S. Pat. Nos. 4,298,162; 4,566,873; 4,731,182; 4,790,806; 4,825,541; 5,047,004; 5,178,602; 5,257,968; 5,261,869; 5,267,936; 5,342,279; 7,156,801; 8,152,708; 8,968,169; and 9,028,387; and U.S. Pat. Appl. Pub. Nos. US2011/0160031 and US2011/0315621). These centrifuges generally share as a centrifuge bowl that can be cylindrical or frustoconical in shape, or that has at least one cylindrical section and at least one frustoconical section, the longitudinal axis of the bowl being generally horizontal. The bowl generally is rotated by means of an electric motor about its longitudinal axis at a speed sufficient to generate a centrifugal acceleration many times that of gravity. A slurry containing a liquid fraction and a solid fraction can be introduced into the interior of the rotating bowl and forms a pond of annular cross section around the peripheral region of the bowl. The heavier particles of the solid fraction are preferentially flung to the walls of the bowl. A scroll mechanism, such as a helical screw, can be mounted inside the bowl and is rotatable about the same longitudinal axis as the bowl. The scroll mechanism can be driven by the same electric motor as the bowl, through a gearbox that can cause the scroll mechanism to rotate at a different speed from that of the bowl, and in a direction that conveys the heavier particles deposited on the wall of the bowl towards one end of the bowl where suitable discharge ports for this fraction are provided. Alternatively, the scroll mechanism can be driven by its own independent motor. In the case in which the bowl has a frustoconical section, the solid fraction is generally discharged at the end of the bowl that has the smaller diameter as this arrangement makes it possible for the solid fraction to be drawn up an inwardly tapering region of the bowl so that some draining of this fraction can take place, and a relatively dry solid fraction can be obtained.

Vacuum System

Preferably, each of the aforementioned filtration options includes a vacuum system capable of drawing a vacuum for removal of solvent. The vacuum system can include a vacuum pump and condenser to prevent organic solvent vapors from reaching the vacuum pump. Condensed vapors arising from the vacuum system condenser are recycled into the solvent recovery system where the organic solvent can be recovered and reused in the process.

Automation

The systems provided herein can be operated either manually or automatically such as by computer control. In some embodiments, the systems and methods herein are automated. In some embodiments, the system includes a computer module for automation of the system. The computer module can be in communication with and/or in control one or more components of the device. In some embodiments, the computer module can be used to modulate the pressure generated by the common vacuum source. In some embodiments, the computer module can be used to modulate the flow of solvent to one or more devices. In some embodiments, the computer module can be used to modulate the temperature of the slurry preparation tank. In some embodiments, the computer module can be used to modulate the speed at which slurry is processed through the product processing system. In some embodiments, the system can be automated by using a programmable logic controller (PLC) and a customizable recipe-driven software architecture. The PLC is the automated programmable device for controlling the process automatically without the need for significant manual intervention. Customizable recipe-driven software allows the process to be tailored to a specific raw material input type and/or processing scheme involving the various optional protein recovery systems illustrated in FIGS. 2-6B.

The PLC can be in direct communication with a control unit, and can be programmable and reprogrammable through the control unit. Logic control allows certain specific actions to occur based upon other actions or conditions. PLCs have the ability to quickly scan inputs and control outputs based upon the condition of the inputs. The inputs can be signals from one or a number of separate meters monitoring the analytical parameters of the system, such as temperature, speed, amount of solvent dispensed, drying temperature, heating temperature, etc. These parameters generally are monitored by separate discrete instruments. These instruments then send a signal, usually some type of analog signal, to a standard input module on the PLC. The PLC can be programmed for each application, such as for different filtration or extraction devices, and different logic control functions can be programmed into the PLC.

Process

The product recovery systems provided herein can include one of several of the aforementioned optional processes for recovering products derived from animal tissue. In the methods and devices provided herein, the processed slurry can be separated into a liquid phase and a solid phase using these separation systems. Exemplary separation systems include vacuum belt filters, indexing belt filters, rotary drum filters, rotary disc filters, belt press filters, filter presses, horizontal disc filters, leaf filters, belt and drum filters, immersion extraction units, percolating extraction units, screw presses, centrifuge systems or any combination thereof. In one embodiment, solid protein product is recovered using an indexing belt filter, such as a unit manufactured by BHS-Filtration, Charlotte, NC. Belt filter devices are well known in the art (e.g., see U.S. Pat. Nos. 3,943,233; 4,595,501; 4,659,469; 4,861,495; 5,200,557; and 8,697,906). In another embodiment, solid protein product is recovered using an immersion extraction unit, an example of which is one manufactured by Crown Ironworks (Roseville, MN). In another embodiment, solid protein product is recovered using a percolating extraction unit, an example of which is one manufactured by Crown Ironworks (Roseville, MN). In yet another embodiment, solid protein product is recovered using a rotary drum filtration unit, such as those units manufactured by BHS-Sonthofen Inc. (Charlotte, NC) and 3VTech (Bergamo, Italy). In another embodiment, solid protein product is recovered using a decanter centrifuge, such as one manufactured by Alfa Laval Inc. (Richmond, VA) or GEA Westfalia Separator Division of GEA Mechanical Equipment US, Inc. (Northvale, NJ).

The starting material from which protein is to be recovered includes animal tissue. Animal tissue includes eukaryotic cells of various shapes and sizes. Animal cells are further characterized as excluding cell walls which are present in all plant cells. The animal tissue may include, but is not limited to, land and marine animals such as insects, fish, poultry and red meat. In an exemplary embodiment, the starting material includes animal tissue from a piscine animal or marine animal. Suitable examples of the starting material include, but are not limited to, tissue material derived from flesh or eggs from anchovies, arctic char, mackerel, sablefish, herrings, sardines, salmon, hake (cod family), halibut, carp, trout, oysters, krill, squid, shrimp and cuttlefish, and as an optional starting raw material, dried fishmeal or dried fish, or any combinations thereof. In some embodiments, the starting material is maintained at temperatures less than 50° F., preferably less than 45° F., and more preferably less than or equal to 40° F., prior to being processed by the product recovery systems provided herein. The starting material can include animal tissue from fish, and in particular, raw fish. The raw fish should be fresh and handled in a sanitary manner. The quality of the raw material should also be verified. The fish is ground, as explained above (see e.g., grinding unit 100), into pieces prior to mixing with organic solvent and further processing. The ground animal tissue is prepared by dispensing whole raw fish and/or raw fish parts to a grinding unit. The resultant ground material will contain the complete animal components inclusive of tissue, bones, and scales. The ground material is then dispensed into a suitable vessel containing an organic solvent.

A finely ground raw fish, such as those materials with a resultant particle size of less than 5000 μm, demonstrates improved filtration characteristics over an otherwise coarsely ground material, such as a material having a particle size greater than 5000 μm. The improved filtration is evident on the belt filter system where the filtration time is significantly faster for finely ground material in comparison to a ground fish material having a particle size greater than 5000 μm. An organic solvent is generally used in the process. The solvent may include an alcohol. In some embodiments, the solvent may include one or more organic solvents with a VOC ranging between about 200-500 g/L. In some embodiments, the solvent is selected such that it meets VOC regulations promulgated by local governing authority. In a preferred embodiment, the solvent includes or is IPA (isopropyl alcohol).

In some embodiments, fishmeal can be used as the starting material. A mixture of fishmeal and solvent is initially heated; however, a low heat, at a temperature below 75° C., is preferably used so there is no risk of decomposition, as determined by final product analysis measuring the protein content, of the protein product due to thermal degradation effects. The ratio of solvent to fishmeal in the mixture should be in the range of from about 1:1 to about 2:1 so that the fishmeal hydrates into a viscous liquid during processing in the slurry preparation tank, and in particular, the heating process, which is done at a controlled temperature using a variable control system that includes a temperature sensor that is immersed into the contents of the tank and that measures the actual temperature of the mixture. A corresponding temperature feedback controller measures the process temperature and regulates the amount of steam, thermal heating fluid, or electrical wattage that is used to heat the contents of the tank. The temperature controller can modulate a control valve, or wattage regulator, to control the steam, thermal heating fluid, or amperes to achieve a specified temperature setpoint, such as 70° C. to prevent the decomposition and/or denaturation of the protein material associated with the raw fish or fishmeal. By preventing decomposition and/or denaturation of the protein material, the amount of protein recovered generally is greater than 85%. The ratio of animal tissue to solvent will depend on various factors including, but not limited to, the specific animal tissue and solvent used. Where the starting material is raw fish and IPA is used as the organic solvent, the ratio of raw fish in kilograms to IPA in liters ranges from about 1:1 to 1:2.2; or from about 1:1 to 1:2.1; or from about 1:1 to 1:2.0; or from about 1:1 to 1:1.9; or from about 1:1 to 1:1.8; or from about 1:1 to 1:1.7; or from about 1:1 to 1:1.6; or from about 1:1 to 1:1.5; or from about 1:1 to 1:1.4; or from about 1:1 to 1:1.3; or from about 1:1 to 1:1.2; or from about 1:1 to 1:1.1. More preferably the ratio is about 1:2. In a preferred embodiment of the present invention, upon scale-up, about 5,000 Kg of raw fish and about 10,000 L of organic solvent are combined to form the mixture of raw fish and solvent.

As illustrated in FIG. 1, a slurry mixture of animal tissue and organic solvent is prepared, where it is heated in the slurry tank, with agitation at a temperature ranging from about 25° C. to about 72° C. The slurry tank includes a primary agitator assembly and a heating source for providing thermal energy to the tank in order to adjust the temperature of the slurry mixture in the slurry tank. The primary agitator assembly, which consists of a rotating mixing shaft with blades, where the mixing blades are rotated by an overhead motor to achieve uniform mixing in the tank, ensures uniform mixing and heating, thus eliminating localized thermally heated zones in the tank that are in contact with the animal tissue and organic solvent mixture, particularly that portion of the mixture in proximity of the heated walls or bottom of the slurry preparation vessel. Such localized contact with thermally hot zones can induce decomposition and/or denaturing of the protein. In ensuring a thermally stable and adequately mixed environment in the slurry tank, protein conforming to the product specification will be recovered, specifically with 85% or higher protein content, as characterized by the resultant amino acid profile conducted through final product analysis.

The heating source can include a jacket encompassing at least a portion of the tank through which a thermal heating fluid, such as steam or heated oil, can be circulated or pumped; or an immersion heater that can be inserted directly into the slurry; or electrical heating elements that are in thermal communication with at least a portion of the tank; or any combination thereof. The slurry tank also can include a jacketing and insulation system to permit cooling of the tank. In some embodiment, the slurry tank includes a jacketing and insulation system that can heat and cool the tank. The slurry tank also can include a variable control system that includes a temperature sensor that is immersed into the contents of the tank and that measures the actual temperature of the mixture. The slurry tank also can include a temperature feedback controller to regulate the amount of thermal energy provided to the tank to adjust the temperature of the slurry. In some embodiments, the temperature feedback controller regulates the amount of steam, thermal heating fluid, or electrical wattage that is provided to the heating source used to heat the contents of the tank. For example, the temperature controller can modulate a control valve, or wattage regulator, or a combination thereof, to control the steam, thermal heating fluid, or amperes available to the heating source.

After processing in the slurry tank, the slurry is then transferred to a dewatering system where it undergoes dewatering to reduce the amount of water present. The dewatering system then transfers the processed slurry to the one of the 5 optional filtration extraction units.

The animal tissue may be fed by the dewatering system back into the slurry preparation tank for further processing before directing the processes slurry to a filtration extraction unit. As discussed above, the slurry preparation tank can include an agitator, as well as a jacketing and insulation system to permit external heating and cooling. Preferably, the mixture is heated to a temperature not exceeding 75° C., for example, about 25-72° C. The resulting homogeneous slurry mixture is then transferred to the dewatering system and then to a filtration extraction unit of the product processing system provided herein. The product processing system, in some embodiments, includes one of a belt filtration system (an example of which is shown in FIG. 2), a rotary drum filter (an example of which is shown in FIG. 3), an immersion extractor (an example of which is shown in FIG. 4), a percolation extractor (an example of which is shown in FIG. 5, or a screw press system (an example of which is shown in FIG. 6), or any combination thereof.

In the systems provided herein, the protein material is filtered and washed. In some embodiments, a countercurrent washing is used. In some embodiments, a countercurrent washing system using captured filtrate is used, followed by a final fresh solvent wash. The final solvent wash can use fresh, virgin solvent, or can use solvent recovered from the system, such as by the SLR system, or a combination of the two. The recovered protein product wetcake is then dried, preferably using heat and vacuum. The nature of the continuous conveyor and filtration systems has the result of substantially increased production throughput. Continuous filtration options allow the process to be automated and to operate in closed circuit, e.g., closed system. The system also can be operated manually. In some embodiments, at least one process of the system is automated.

The low-moisture wetcake product recovered from the product processing system is further dried in a dryer and discharged from the dryer and into a particle reduction system where a micronized particle size for the product is established in the range of less than 75 µm to 250 µm. The resultant powdered protein product is then transferred to a product receptacle. The powdered protein product can be analyzed to establish whether the protein product conforms to target specifications. In an exemplary embodiment, the yield of solid protein is from about 10 wt % to about 25 wt % based upon the starting weight of the raw animal tissue starting material. Preferably, the yield of protein is in the range of from about 10 wt % to about 18 wt % based upon the starting weight of the animal tissue entering the grinding unit. In some embodiments, the yield of protein is greater than about 15 wt % based upon the starting weight of the animal tissue.

A laboratory analysis of the powdered protein product from the product recovery systems provided herein showed that the recovered powdered protein product has a protein concentration in the range from about 80 wt % to about 95 wt %, generally from about 85 wt % to about 95 wt %. An amino acid profile identifies the amino acids present in a product depending on the type of animal tissue. The recovered powdered protein product can be a complete protein, non-hygroscopic, and substantially free of fish odor or smell contributed by amines, particularly volatile amines. The recovered powdered protein product can also be non-hygroscopic and sterile, and visually, the protein can exhibit a cream color. The typical composition profile of the final powdered protein product shows that the protein includes all of the essential and non-essential amino acids. The final product has very low fat and cholesterol levels, negligible heavy metals residue, has over 95% digestibility, and is non-hygroscopic. Additional constituents include natural fish essential minerals, such as calcium and collagen, phosphorous, selenium, sodium, zinc, magnesium, iron, and copper.

The final product has an extremely mild flavor and aroma, and is non-gelling. The product serves as an excellent source of dietary supplements and protein meal replacement products. In addition, the final product does not degrade over time, as the process is low temperature, e.g., not exceeding 80° C., in order to prevent thermal degradation of the protein. The organoleptic properties (i.e. smell and taste), amino acid profile, and concentration of protein of the final product are stable upon long term storage. The amount of protein in the final product can vary from about 40 wt % to about 99 wt %, such as at least 50 wt %, or at least 60 wt %, or at least 70 wt %, or at least 80 wt %, or at least 90 wt % are stable upon long term storage. The final product exceeds all FDA requirements for a supplement and is an excellent product for world food needs.

In the processes provided herein, the raw starting material generally is mixed with a food grade solvent, such as ethanol or IPA, at concentrations that can act as a disinfectant or an anti-bacterial during many stages of the process. The separated solid material containing the protein component can be in contact with at least some amount of the food grade solvent throughout the process, making material and equipment handling easier and making maintenance of sanitary conditions throughout the process easier. This can insure that the finished protein product and omega-3 oil product obtained using the processes provided herein are sanitary and safe for human consumption.

The final product also has a long shelf life of at least 5 years as determined by maintaining a fairly constant analytical profile from the time of its original manufacturing. In one embodiment, the recovered solid protein product was tested in a laboratory simulating environmental conditions over 10 years. The constant profile may be attributed to the final product's non-hygroscopic, or substantially non-hygroscopic, nature. That is, because the final product does not absorb humidity, it maintains a low water activity that prevents bacteriological growth. Preferably the moisture content of the final product is less than about 8 wt %. The recovered protein has amino acid compositions that are balanced to afford a nutritionally advantageous characteristic.

In the methods and systems provided herein, the filtrates that are extracted as a result of the process recovery system, which can use any filtering system, such as a belt filtration system, a rotary drum filter, an immersion extractor, a percolation extractor, or a screw press, or combinations thereof, are transferred to the solvent liquid recovery system (SLR). The SLR includes an adsorber system and a carbon filtration system. The filtrate can include, but is not limited to, oils, fats, solvent and water. When the animal tissue is fish, the oil can include omega-3 fatty acids. In the SLR system, the filtrate can first be transferred to an adsorber system, then to a carbon filtration system and, optionally, subsequently filtered once again to remove residual solids. In some embodiments, the adsorber system includes a fixed, packed bed column containing resin particles or beads. The particular resin beads will have an affinity for free amines and miscellaneous undesired hydrocarbons that can be present in the filtrate. The filtrate is transferred through the adsorber system, and the resultant stream that exits the adsorber system will be purified via treatment using the carbon filtration system. The adsorption process generally is done at ambient temperature. In some embodiments, a pump can be used to pump the filtrate through the adsorber system.

The stream leaving the adsorber system can be directed to the carbon filtration system. The carbon filtration is also a fixed bed operation and is used as polishing step following the adsorber process. Alternatively, the stream leaving the adsorber system can be directed directly to a solvent recovery system, which can include a distillation tower or a centrifuge or both, in order to separate the organic solvent/water from oils/fats. The solvent can be separated from water to yield a recovered organic solvent, which can be transferred to a recovery tank, and thereafter, used as recycled organic solvent in the methods and systems provided herein.

The recovered oils, for example, omega-3 fatty acids, can be filtered to remove residue and to increase the purity thereof. The recovered oils also can be treated with activated carbon to remove the odor by neutralizing any amines present in the oil. The residue produced can be separated from the oil and transferred to a discarding tank. The oils, including omega-3 fatty acids, can be transferred to a first recovery tank. There, the oil can undergo further purification via molecular distillation and/or transesterification. The recovered oils including omega-3 fatty acids are polyunsaturated fatty acids with a double bond on the end of the carbon chain. They are considered essential fatty acids. Humans cannot readily make omega-3 fatty acids in their bodies, and therefore it must be obtained from other sources since omega-3 fatty acids play an important role for normal metabolism.

In an exemplary embodiment, omega-3 fatty acids are recovered in amounts greater than or equal to about 5 wt % based on the weight of the original animal tissue feedstock. Preferably omega-3 fatty acids are recovered in amounts of greater than or equal to 6 wt % of the original animal tissue feedstock. More preferably, omega-3 fatty acids are recovered in amounts greater than or equal to 7 wt % of original animal tissue feedstock. The level and composition of fatty acids and omega-3 oils contained in raw fish are a function of the fish species and their origin of habitat.

In yet another embodiment, the organic solvent/water independently can be recovered using the solvent/liquid recovery (SLR) system, e.g., by using extractive distillation. Namely, a third component can be introduced into the process. For example, when isopropyl alcohol (IPA) is the organic solvent, diisopropyl ether (IPE) can be used, whereby IPA and IPE combine to completely separate water from the IPA. The IPA/IPE mixture is then further distilled in a secondary distillation column to recover IPA. The IPA then can be transferred to a recovery tank for further processing as discussed above. The water can be recovered for human consumption and/or industrial applications. The recovered water contains few or no ions.

Recovered Low-Moisture Wetcake

In some embodiments of the methods and systems provided herein, the protein product wetcake can be withdrawn from product separation system 10 via outlet O. The protein product wetcake discharged via outlet O can contain at least about 50 wt % protein. In some embodiments, the protein product wetcake can contain impurities or omega-3 oil. In some embodiments, the protein product wetcake contains no or less than 0.1% of any one impurity. In some embodiments, the protein product wetcake contains 0.1% or less, or 0.05% or less fat. In some embodiments, the protein product wetcake is free of any fish odor. In some embodiments, the protein product wetcake is odorless. In some embodiments, the protein product wetcake is free of cholesterol. In some embodiments, the protein product wetcake is free of sugar. In some embodiments, the protein product wetcake can be a washed wetcake or an optionally enriched wetcake or a washed, enriched wetcake.

The protein product wetcake can be dried in a dryer unit 800 to further reduce the amount of moisture and/or residual organic solvent present in the washed wetcake or washed and enriched wetcake. The dried protein product wetcake can be recovered at outlet 820 into a packaging device 830. The type and configuration of the dryer unit 800 can be selected to optimize the amount of moisture and/or organic solvent removed without negatively impact protein product quality. For example, forced air, direct IR, indirect IR or convection ovens can be used to directly or indirectly dry the wetcake. Additional drying units can include a tray drying system, rotary cone vacuum dryer, fluid bed dryer or spray drying unit. In some embodiments, the wetcake is dried to a moisture content of about 10 wt % or less, or about 5 wt % or less, and a residual organic solvent content of about 1 wt % or less, or 0.5% or less under full vacuum at a temperature of 100° C. or less, such as 80° C. or less.

The dried wetcake can be stored as wetcake, or can be milled into small particle sizes using a milling unit. In some embodiments, the product recovery system 1000 provided herein can include a mill unit 815 for milling the dried wetcake. Examples of mills that can be incorporated into the system include, but are not limited to, a Micronizer® jet mill or Powderizer® mill or Simpactor® mill (each of which is available from Sturtevant, Inc., Hanover, MA), a hammer mill, a roll crusher or a rotary crusher. The dry powdered protein product 825 can be recovered from mill unit 815 via mill outlet 820 and stored in packaging device 830.

EXAMPLES

The following examples illustrate specific aspects of the present invention. The examples are not intended to limit the scope of the present invention.

Pepsin Analysis

A powdered protein recovered from fish was prepared using the system and methods provided herein. A typical analytical profile for the powdered protein product showed that the yield of protein from the fish starting material was 85.4%, the moisture content of the dried powdered protein product was 7.68%, and crude fat content was 1.42%. The recovered powdered protein product derived from fish was tested using the well-known pepsin test (0.2% pepsin, AOAC method 971.09) to assess the quality of the protein. Pepsin is an enzyme that is used to digest protein structures. The pepsin test is used to determine how much protein is within a mixture. The powdered protein product sample was defatted and digested with a 0.02% solution of pepsin for 16 hours. The resultant digest was filtered and washed to isolate the indigestible residue, which is then analyzed for protein. The "Pepsin Digestible Protein" then can be calculated as a percentage of the crude protein by the relationship (crude protein−indigestible protein)/crude protein=Pepsin Digestible Protein. The recovered powdered protein product derived from fish had over 98% digestible protein.

The sample also was tested for trans fatty acid and cholesterol. The amount of trans fatty acid isomers was less than 0.1 wt. % of a 100 g serving, and the amount of cholesterol was less than 0.05 wt. % of a 100 g serving.

Mineral Content Comparison

The powdered protein product was analyzed for mineral content. An elemental scan of the product showed that the powdered protein product is a good source of calcium, iron, magnesium, zinc, and phosphorus, while having low levels or sodium and potassium. The results are shown in Table 3. Table 3 shows the amount of the listed elements in a 25 g sample of one example of the recovered powdered protein product derived from fish using the process and methods described herein. The amounts are shown as a percentage of the recommended daily allowance (RDA) for the mineral. Also shown are the amounts of the listed elements in a 25 g sample of commercial protein powders on the market.

Notably, the calcium, iron and zinc contents of 25 mg APP is significantly greater than for each of DFH whey, JF whey, GNC whey, Whey Isolate, Whey concentrate, JF soy and NB soy. The amount of iron present in APP is significantly greater than in each of DFH whey, JF whey, GNC whey, Whey Isolate, and Whey concentrate.

TABLE 5

Comparative mineral content.
Comparing mineral content per 25 grams of protein as a percentage of the RDA

| | Powdered Protein Product | DFH whey | JF whey | GNC whey | Whey Isolate | Whey conc. | JF soy | NB soy |
|---|---|---|---|---|---|---|---|---|
| Calcium | 55% | 12.5 | 9.0% | | 8.3% | 18.8% | 2.9% | 5.0% |
| Iron | 18.1% | 4.2% | 1.8% | | | | 22.2 | 22.2% |
| Magnesium | 10% | | 3.5% | | | | | 2.8% |
| Zinc | 9.8% | | | | | | | 6.7% |
| Sodium | 2.1% | 2.0% | 1.7% | 2.6% | 2% | 2.3% | | 0.6% |
| Potassium | 4.6% | 4.6% | 3.7% | 5.7% | 8.7% | 3.7% | 10.6 | 12.9% |
| Phosphorus | 18.4% | 21.3 | 8.9% | | | | | 29.3% |

It will be understood by one skilled in the art that each of the above-described embodiments, as well as any sub-parts of those embodiments, can be operated in a continuous or a non-continuous manner. Non-continuous operations include, but are not limited to, batch-wise operations, cyclical operations, and/or intermittent operations. Additionally, it will be understood that two or more of the above embodiments can be used in combination.

It will be apparent to those skilled in the art that various modifications and variation can be made in the present invention without departing from the spirit or scope of the invention. Thus, it is intended that the present invention cover the modifications and variations of this invention provided are within the scope of the appended claims and their equivalents.

| LIST OF FIGURE ELEMENTS | |
|---|---|
| I | Inlet to filtration system 10 |
| O | Outlet of filtration system 10 |
| 3 | Product Wash stream |
| 5 | Recycle feed stream |
| 7 | Drying gas |
| 10 | Product separation system |
| 15 | Product wash inlet |
| 25 | Process filtrates outlet line |
| 27 | Drying gas inlet |
| 30 | Discharge stage |
| 35 | Wetcake transport line |
| 40 | Common vacuum source |
| 45 | Vapor condenser |
| 47 | Outlet from vapor condenser |
| 80 | Common vacuum line |
| 100 | Grinding unit |
| 105 | Discharge line from grinding unit |
| 150 | Slurry preparation tank |
| 155 | Preparation tank outlet |
| 170 | Dewatering device |
| 171 | Dewatering device outlet |
| 173 | Return line to feed prep tank |
| 175 | Processed slurry line to filtration system |
| 177 | Press liquid outlet line |
| 180 | Solvent Supply tank |
| 185 | Virgin solvent line to prep tank |
| 189 | Virgin solvent line to filtration system |
| 200 | Belt filtration system |
| 201 | Beginning belt roller |
| 202 | Ending belt roller |
| 211 | Pump from 221 |
| 212 | Pump from 222 |
| 213 | Pump from 223 |
| 214 | Pump from 224 |
| 215 | Pump from 225 |
| 220 | Conveyor belt filter |
| 221 | Receiver from box 251 (stage 1) |
| 222 | Receiver from box 252 (stage 2A) |
| 223 | Receiver from box 253 (stage 2B) |
| 224 | Receiver from box 254 (stage 2C) |
| 225 | Recycle receiver (from box 255, stage 3) |
| 231 | discharge line from box 251 |
| 232 | discharge line from box 252 |
| 233 | discharge line from box 253 |
| 234 | discharge line from box 254 |
| 235 | discharge line from box 255 |
| 236 | discharge line from box 256 |
| 241 | line from pump 211 |
| 242 | line from pump 212 |
| 243 | wash line from pump 213 to 262 |
| 244 | wash line from pump 214 to 263 |
| 245 | wash line from pump 215 to 265 |
| 251 | vacuum box of stage 1 |
| 252 | vacuum box of stage 2A |
| 253 | vacuum box of stage 2B |
| 254 | vacuum box of stage 2C |
| 255 | vacuum box of stage 3 |
| 256 | vacuum box of stage 4 |
| 262 | applicator X (to stage 2A, box 252) |
| 263 | applicator Y (to stage 2B, box 253) |
| 264 | applicator Z (to stage 2C, box 254) |
| 265 | applicator R (recycle stage 3, box 255) |
| 270 | Product wash feed line |
| 275 | Stage 1 applicator |
| 280 | Outlet |
| 290 | Processed slurry supply line |
| 300 | Drum filtration system |
| 301 | Slurry inlet |
| 310 | Housing |
| 312 | Rotary drum filter |
| 314a | Seal |
| 314b | Seal |

-continued

| | LIST OF FIGURE ELEMENTS | |
|---|---|---|
| 314c | Seal | |
| 314d | Seal | |
| 314e | Seal | |
| 314f | Seal | |
| 314g | Seal | |
| 322 | Discharge stage | |
| 324 | Filter wash stage | |
| 326 | Filter cells | |
| 330 | Wash feed inlet | |
| 332 | first wash filtrate inlet | |
| 334 | Second wash filtrate inlet | |
| 336 | Initial wash stage | |
| 338 | Intermediate wash stage | |
| 340 | Final wash stage | |
| 341 | Discharge line (e.g., to 705) | |
| 342 | initial wetcake | |
| 344 | washed wetcake | |
| 346 | washed and enriched wetcake | |
| 348 | recycle feed inlet | |
| 350 | drying gas inlet | |
| 355 | recovered product (low-moisture wetcake) | |
| 360 | Stage 1 - separation stage | |
| 370 | Stage 2 - wash stage | |
| 380 | Stage 3 - optional recycle stage | |
| 385 | Discharge line | |
| 387 | Recycle discharge line | |
| 390 | Stage 4 - drying stage | |
| 395 | Discharge line | |
| 400 | Immersion extraction unit | |
| 405 | Entry port | |
| 407 | Processed slurry | |
| 410 | Solvent bath | |
| 415 | Upper level of solvent bath 410 | |
| 421 | Conveyor belt | |
| 422 | Conveyor belt | |
| 423 | Conveyor belt | |
| 424 | Conveyor belt | |
| 425 | Conveyor belt | |
| 430 | Belt protrusions | |
| 440 | Solvent wash applicator | |
| 450 | Discharge port | |
| 490 | Discharge line (e.g., to 30) | |
| 495 | Filtrate outlet line (e.g., to 705) | |
| 500 | Percolation extraction system | |
| 505 | entry port | |
| 510 | Pump | |
| 511 | Pump | |
| 512 | Pump | |
| 513 | Pump | |
| 514 | Pump | |
| 520 | Filtrate outlet to pump 510 | |
| 521 | Filtrate outlet to pump 511 | |
| 522 | Filtrate outlet to pump 512 | |
| 523 | Filtrate outlet to pump 513 | |
| 524 | Filtrate outlet to pump 514 | |
| 540 | Conveyor belt | |
| 542 | Belt protrusions | |
| 545 | Stationary screen | |
| 550 | Motor assembly | |
| 560 | Filtrate receiving compartment | |
| 561 | Filtrate receiving compartment | |
| 562 | Filtrate receiving compartment | |
| 563 | Filtrate receiving compartment | |
| 564 | Filtrate receiving compartment | |
| 571 | Spray applicator | |
| 572 | Spray applicator | |
| 573 | Spray applicator | |
| 580 | Wash applicator | |
| 585 | Discharge line (from pump 514) | |
| 590 | Exit | |
| 595 | Discharge line (from pump 510) | |
| 600 | Screw press system | |
| 601 | Motor | |
| 603 | Gear reduction drive | |
| 605 | Shaft coupling | |
| 610 | Inlet port | |
| 615 | Screen chamber | |

-continued

| | LIST OF FIGURE ELEMENTS | |
|---|---|---|
| 618 | Solids restrainer | |
| 620 | Liquid drain | |
| 625 | Press cake discharge | |
| 630 | Frame | |
| 635 | Screw | |
| 640 | Continuous feeder flighting | |
| 645 | Gear box | |
| 650 | Screw shaft | |
| 655 | Restraining cone | |
| 660 | Adjuster | |
| 675 | Decanter Centrifuge | |
| 700 | Solvent/liquid recovery (SLR) system | |
| 705 | Liquid phase processing unit | |
| 710 | Processer outlet line | |
| 715 | Separation unit | |
| 720 | Recovered solvent transfer line | |
| 725 | Recovered oil transfer line | |
| 730 | Omega-3 oil | |
| 740 | Recovered solvent tank | |
| 745 | Recovered solvent line to slurry tank | |
| 750 | Recovered solvent line to wash inlet | |
| 760 | Waste outlet | |
| 765 | Waste outlet line | |
| 770 | Purified water outlet | |
| 775 | Purified water | |
| 800 | Dryer unit | |
| 810 | Dryer unit outlet | |
| 815 | Milling unit | |
| 820 | Mill outlet | |
| 825 | Dry powdered protein product | |
| 830 | Packaging device | |
| 840 | Vapor Condenser | |
| 845 | Condenser outlet | |
| 1000 | Product recovery system | |

What is claimed is:

1. A system for obtaining a protein product powder, the system comprising:
    a) a slurry preparation unit for preparing a slurry;
    b) a product separation system for separating the slurry into a liquid phase and a solid phase, the product separation system comprising a continuous conveyance filtration system, wherein the continuous conveyance filtration system is a belt filtration system, and wherein the belt filtration system comprises a path;
    c) one or more vacuum boxes disposed on said path; and
    d) a counter-current recycled filtrate wash stage.

2. The system of claim 1, further comprising a drying unit for reducing a moisture content of the solid phase to produce a dried protein product, wherein the drying unit is disposed on the continuous conveyance filtration system.

3. The system of claim 2, further comprising a milling unit for producing the protein product powder from the dried protein product.

4. The system of claim 1, wherein the system is automated.

5. The system of claim 4, wherein the system comprises a programmable logic controller.

6. The system of claim 1, further comprising a separation unit that separates the liquid phase into one or more components selected from the group consisting of a recovered solvent, water and omega-3 oil, wherein the separation unit comprises a distillation unit, a centrifugation unit, or any combination thereof.

7. The system of claim 1, further comprising a liquid phase processing unit for receiving the liquid phase from the product separation system, wherein the liquid phase processing unit comprises an adsorber system and/or an activated carbon filtration system.

8. The system of claim 1, wherein the slurry preparation unit comprises a preparation tank for receiving and mixing a raw material with a solvent to form the slurry.

9. The system of claim 1, further comprising a variable frequency drive (VFD) that modulates speed of the continuous conveyance filtration system.

10. The system of claim 1, configured for installation on a marine vessel.

\* \* \* \* \*